United States Patent
Sano

(10) Patent No.: US 9,330,896 B2
(45) Date of Patent: May 3, 2016

(54) MASS ANALYSIS DEVICE AND MASS SEPARATION DEVICE

(71) Applicant: Yoshinori Sano, Tokyo (JP)

(72) Inventor: Yoshinori Sano, Tokyo (JP)

(*) Notice: Subject to any disclaimer, the term of this patent is extended or adjusted under 35 U.S.C. 154(b) by 0 days.

(21) Appl. No.: 14/430,788

(22) PCT Filed: Sep. 24, 2013

(86) PCT No.: PCT/JP2013/075780
§ 371 (c)(1),
(2) Date: Jul. 14, 2015

(87) PCT Pub. No.: WO2014/050836
PCT Pub. Date: Apr. 3, 2014

(65) Prior Publication Data
US 2015/0357176 A1    Dec. 10, 2015

(30) Foreign Application Priority Data

Sep. 25, 2012  (JP) ................................. 2012-210600
Apr. 10, 2013  (JP) ................................. 2013-082405

(51) Int. Cl.
| | |
|---|---|
| B01D 59/44 | (2006.01) |
| H01J 49/34 | (2006.01) |
| H01J 49/40 | (2006.01) |
| H01J 49/00 | (2006.01) |
| H01J 49/06 | (2006.01) |
| G01N 27/62 | (2006.01) |

(52) U.S. Cl.
CPC .............. *H01J 49/401* (2013.01); *G01N 27/62* (2013.01); *H01J 49/0086* (2013.01); *H01J 49/061* (2013.01); *H01J 49/067* (2013.01); *H01J 49/408* (2013.01)

(58) Field of Classification Search
USPC ...... 250/281, 282, 287, 292–295, 396 R, 526
See application file for complete search history.

(56) References Cited

U.S. PATENT DOCUMENTS 7,196,327 B2 * 3/2007 Thomson .............. H01J 49/025
                                                      250/281
8,389,929 B2 * 3/2013 Schoen .................. H01J 49/26
                                                      250/281
(Continued)

FOREIGN PATENT DOCUMENTS

JP    2-270256    11/1990
JP    5-174783    7/1993
(Continued)

OTHER PUBLICATIONS

International Search Report of PCT/JP2013/075780 dated Dec. 3, 2013 (8 pages total) English language translation provided.
(Continued)

*Primary Examiner* — Bernard E Souw
(74) *Attorney, Agent, or Firm* — Hamre, Schumann, Mueller & Larson, P.C.

(57) ABSTRACT

An object of the present invention is to provide a mass spectrometer and a mass separator whose design and performance are less restricted by problems arising from the principle of operation, and which have in principle no limitation on the mass-to-charge ratio range to be able to deal with and are each capable of repeatedly analyzing or extracting plural ionic species of different mass-to-charge ratios in a short time.

A mass spectrometer (10) is configured from an ion source (1), an ion introduction unit (2), a mass analyzer (3), an ion detection unit (4), and the like. Crude ions are introduced into a separation space (5) at a predetermined acceleration voltage as a pulse synchronized with the phase of a one-dimensional high-frequency electric field. In the separation space (5), each ion travels in an incident direction by inertia, and besides they are displaced by force received from the one-dimensional high-frequency electric field which acts in the y-direction crossing the incident direction. Ionic species having different mass-to-charge ratios with each other are separated by the difference in displacement magnitude. At this time, the acceleration voltage and the period of the one-dimensional high-frequency electric field are set in order that the measured ionic species may exit from the separation space (5) having received the action of the electric field for one period.

11 Claims, 13 Drawing Sheets

(56) References Cited

U.S. PATENT DOCUMENTS

| | | | | |
|---|---|---|---|---|
| 2005/0056778 A1* | 3/2005 | Thomson | ............... | H01J 49/025 250/288 |
| 2011/0215235 A1* | 9/2011 | Schoen | ................... | H01J 49/26 250/282 |
| 2014/0374617 A1* | 12/2014 | Kabasawa | ............... | H01J 37/05 250/396 R |

FOREIGN PATENT DOCUMENTS

| | | |
|---|---|---|
| JP | 2005-536021 | 11/2005 |
| JP | 2010-108941 | 5/2010 |
| WO | 2004/017358 | 2/2004 |
| WO | 2011/109311 | 9/2011 |

OTHER PUBLICATIONS

Toyoda, "Shitsuryō-bunseki," in "Zikken-kagaku Kōza 20-1; Bunseki-kagaku," 5th ed, ed by The Chemical Society of Japan, Maruzen, 2007, Chap. 9, 14 pages total.

Gross, "Mass Spectrometry; A Textbook", Springer-Verlag, 2007, 53 pages total.

de Hoffmann et al., "Mass Spectrometry; Principles and Applications", Wiley-Interscience, 2007, 10 pages total.

Fuwa et al., "Shijūkyoku Shituryō-bunseki-kei; Genri to Ōyō", Kōdansha, 1977, 2 pages total.

* cited by examiner

MASS ANALYSIS DEVICE AND MASS SEPARATION DEVICE

TECHNICAL FIELD

The present invention relates to a mass spectrometer and a mass separator which use a one-dimensional high-frequency electric field for mass separation of ions.

BACKGROUND ART

In mass spectrometry, we ionize an analyzed sample by a suitable method, separate generated ions based on the difference in the mass-to-charge ratio, and detect them qualitatively or quantitatively by their respective mass-to-charge ratios. By this method we can get information about the composition and the structure of the analyte. Here, we define the term, mass-to-charge ratio of a given ion, as follows, and use it throughout the present Description. Its mass m is divided by the atomic mass constant ($1/12$ of the mass of one atom of $^{12}C$) to yield its exact relative mass, which is further divided by its charge number $z_i$. The resultant dimensionless number is its mass-to-charge ratio.

A mass spectrometer consists of an ion source, an ion introduction unit, a mass analyzer, an ion detection unit, etc., and a passage of ions is in high vacuum at least in the mass analyzer and around it. The mass analyzer separates ionic species having different mass-to-charge ratios with each other by the difference in their motion in the vacuum. Most of spectrometers of general use which are now on the marcket have one of three types of mass analyzers described below (see Non patent Literature 1-4). Hereafter, we use the term, crude ions, to refer to a crowd of ions which is dealt with as a group at various locations in a mass spectrometer, in order to distinguish from one ion or merely plural ions. We also use the term, initial state, to refer to a kinetic state of an ion in the ion source before extraction by an acceleration voltage. Furthermore, we use symbol e which represents the elementary charge, and use the International System of Units (SI) as units for physical quantities unless we explicitly state otherwise.

<Time-of-Flight (TOF) Mass Analyzer>

In a TOF mass analyzer, pulsed crude ions are extracted from an ion source by a predetermined acceleration voltage U, and are introduced into a field-free drift path of known length $L_F$. From the velocity of each ion v, the time $T_F$ needed for the ion to travel through this path is given by the next formula $T_F = L_F / v$.

Hence the TOF analyzer functions as a velocity analyzer.

<Magnetic Sector Mass Analyzer>

In a magnetic sector mass analyzer, crude ions are extracted from an ion source by a predetermined acceleration voltage U. Then these ions are introduced into a magnetic sector analyzer, perpendicular to a homogeneous magnetic field of the magnetic flux density B. In the magnetic field the flight direction of each ion is continuously altered by the Lorentz force. Consequently, the ion travels on a circular path of a radius R. This radius is given by the next formula $R = mv / z_i eB$.

Hence the magnetic sector analyzer functions as a momentum analyzer.

<Quadrupole Mass Analyzer>

A quadrupole mass analyzer consists of four samely shaped rod electrodes. The quadrupole electric field is produced in the long and slender space surrounded by these electrodes, and this space is used as a passage of ions. Crude Ions are introduced into the passage from one end in the longitudinal direction along with the symmetry axis. Then each ion travels toward the other end by inertia, and besides oscillates by the force received from the electric field. In this time, only an ionic species of a particular mass-to-charge ratio is fit for the electric field, and may travel the passage to the exit end with stable oscillation of limited amplitudes. The other ionic species oscillate with too large amplitudes, and are removed either with hitting the rod electrodes or with flying out between the rod electrodes.

In addition to the above, there are on the market mass spectrometers which have a linear quadrupole ion trap mass analyzer, a three-dimensional quadrupole ion trap mass analyzer, or a Fourier transform ion cyclotron resonance mass analyzer. These ion trapping type devices, however, require somewhat complicated operation for one analysis. This operation consists of introduction, tpapping and ejection of ions. Moreover, since the analysis becomes intermittent, it is not suitable at least for fast real time measurement. Consequently, these mass spectrometers are used mainly for a use in which their ion trapping function is effective.

SUMMARY OF INVENTION

Technical Problem

In the TOF mass spectrometer and the magnetic sector mass spectrometer, crude ions generated in an ion source are extracted by a predetermined acceleration voltage U. Thus the same kinetic energy $z_i eU$ is given to each of them. Then they are introduced into the mass analyzer, where ionic species having different mass-to-charge ratios with each other are separated based on the difference in their velocity and momentum which are brought about by the above kinetic energy in the extracted direction, respectively. In this case, when a kinetic energy which each ion has at the initial state cannot be neglected in comparison to $z_i eU$, its fluctuation restricts the mass resolving power of the spectrometer. Accordingly, in order to lower its influence relatively and to attain higher mass resolution, it is necessary to increase the acceleration voltage U. Consequently, the flight length of ions becomes longer and the instrument size becomes larger.

In the quadrupole mass spectrometer, ionic species of too large mass-to-charge ratios are difficult to maintain stable oscillation, and consequently transmittance is low for them. Furthermore, although the RF (radio frequency) voltage applied to the rod electrodes is necessary to be increased with the increase of the mass-to-charge ratio, there are technical limitations for the increase of the RF voltage due to the voltage endurance, power consumption and so on. If the radio frequency is lowered, it becomes possible to analyze ionic species of large mass-to-charge ratios without the increase of the RF voltage. In this case, however, another problem arises that ionic species of small mass-to-charge ratios pass through the analyzer without oscillating enough times. As a result of these, the upper-limit of the mass-to-charge ratio able to be analyzed is limited to about 2000-4000.

In addition, the existing mass analyzers have not adequate performance to measure repeatedly respective amounts of two or more ionic species of different mass-to-charge ratios in a short time. We describe this problem below.

The quadrupole mass spectrometer and the magnetic sector mass spectrometer can continuously measure the amount of an ionic species in real time. But in principle the quadrupole mass spectrometer cannot measure simultaneously respective amounts of multiple ionic species of different mass-to-charge ratios. The magnetic sector mass spectrometer can measure simultaneously them by using a focal plane detector etc., but the mass-to-charge ratio range is narrow.

In order to compare respective amounts of plural ionic species simultaneously unmeasurable, the scan is required. However, even in the quadrupole mass spectrometer capable of comparatively fast scanning, about 1 ms is needed to scan one species with the selected ion (switching over ion) scan mode, in which some ionic species are selected and detected one after another. The scan is slower in the magnetic sector mass spectrometer. We cannot measure and compare respective amounts of plural ionic species within a time shorter than these scanning times.

Consequently, quantitative accuracy tends to be easily lowered in these mass spectrometers. For example, let us consider the case that there is fluctuation in the ionization conditions such as the analyte gas pressure, the energy putted in for ionization, etc. Even if we measure respective amounts of an analyte ionic species and an internal standard ionic species by the scan, and correct the fluctuation by calibration based on the internal standard, fluctuation arising within the scanning time are not compensated.

Furthermore, correct relations among respective amounts of plural ionic species cannot be known in the system whose composition changes within the scanning time. Consequently, the performance to follow the change of the system tends to be inadequate. It occurs when fast chemical reactions take place, and when multiple components elute imperfectly separated in a gas chromatograph-mass spectrometer (GC-MS) or a liquid chromatograph-mass spectrometer (LC-MS), and so on.

On the other hand, in the TOF mass spectrometer, in principle a complete mass spectrum is obtained from each introduction of pulsed crude ions. Hence, the calibration based on the internal standard is possible, and the correct relation among respective amounts of plural ionic species can be known. One analysis, however, requires the time in which all ions tavel through the drift path, namely, at least 100 µs, usually several-several ten milliseconds. Consequently, the change of the system cannot be followed at an interval shorter than this time.

It is difficult to solve the above described problems by any partial improvement, because they arise from the principle of operation of each mass analyzer.

The present invention has been accomplished to solve the above described problems. Its object is to provide a mass spectrometer and a mass separator whose design and performance are less restricted by problems arising from the principle of operation, and which have in principle no limitation on the mass-to-charge ratio range to be able to deal with and are each capable of repeatedly analyzing or extracting plural ionic species of different mass-to-charge ratios in a short time.

Solution to Problem

The present invention provides a mass spectrometer comprising at least:

an ion source having a means to ionize a sample, and a means to introduce pulsed crude ions into a mass analyzer by a predetermined acceleration voltage;

an ion introduction unit having a means to focus the flight directions of said crude ions, and/or a means to select out said crude ions which travel toward predetermined directions;

said mass analyzer which has a separation space where said crude ions introduced travel and a means to produce in said separation space a one-dimensional high-frequency electric field that acts in the direction (hereafter referred to as y-direction) crossing the incident direction of said crude ions at a predetermined angle, and makes the ionic species having different mass-to-charge ratios with each other travel on different flight paths through the action of said one-dimensional high-frequency electric field;

an ion detection unit having a means to detect ions which come to the predetermined position in the y-direction on the exit plane at the end of said separation space;

wherein said crude ions are introduced into said separation space as a pulse synchronized with the phase of said one-dimensional high-frequency electric field, and the measured ionic species of a predetermined mass-to-charge ratio(s) exits from said separation space having received the action of said one-dimensional high-frequency electric field for n periods or for the substantially same time as it, and is detected in distinction from the other ionic species based on the position in the y-direction on said exit plane. (Here, n stands for a natural number.)

The present invention also provides a mass separator comprising at least:

an ion source having a means to ionize a sample, and a means to introduce pulsed crude ions into a mass analyzer by a predetermined acceleration voltage;

an ion introduction unit having a means to focus the flight directions of said crude ions, and/or a means to select out said crude ions which travel toward predetermined directions;

said mass analyzer which has a separation space where said crude ions introduced travel and a means to produce in said separation space a one-dimensional high-frequency electric field that acts in the direction (hereafter referred to as y-direction) crossing the incident direction of said crude ions at a predetermined angle, and makes the ionic species having different mass-to-charge ratios with each other travel on different flight paths through the action of said one-dimensional high-frequency electric field;

an ion selection unit having a means to extract ions which come to the predetermined position in the y-direction on the exit plane at the end of said separation space;

wherein said crude ions are introduced into said separation space as a pulse synchronized with the phase of said one-dimensional high-frequency electric field, and the selected ionic species of a predetermined mass-to-charge ratio(s) exits from said separation space having received the action of said one-dimensional high-frequency electric field for one period or for the substantially same time as it, and is extracted in distinction from the other ionic species based on the position in the y-direction on said exit plane.

In the present invention, we use the term, high-frequency electric field, to refer to an alternating current (AC) electric field which has an arbitrary waveform and whose period is equal to or shorter than 2 ms. In the AC electric field, the impulse which acts on an ion from the electric field becomes 0 for one period. In relation to the essence of the present invention, we also use each term, the measured ionic species and the selected ionic species, not to refer to an ionic species which is merely detected or selected, but to refer to an ionic species which exits from said separation space having received the action of said one-dimensional high-frequency electric field for n periods or one period respectively, or for the substantially same time as it, and is detected or selected. Here, the term, substantially, means that some increases and decreases or errors are allowed according to device performance such as required mass resolving power, within the range that gives no change of the essence of the present invention.

Advantageous Effects of Invention

In the mass spectrometer of the present invention, said crude ions are introduced from said ion source into said separation space at said predetermined acceleration voltage. Then, each ion travels in said incident direction by inertia, and besides they are displaced in said y-direction by the force received from said one-dimensional high-frequency electric field which acts in the direction (said y-direction) crossing said incident direction. This displacement differs from the uniformly accelerated motion in a static electric field, and its magnitude is inversely proportional to the mass-to-charge ratio of the ion. Though this magnitude also varies depending on a phase at which said one-dimensional high-frequency electric field begins to act on the ion, it is kept constant if the phase is held constant. Therefore, when said crude ions are introduced into said separation space as a pulse synchronized with the phase of said one-dimensional high-frequency electric field, the ionic species having different mass-to-charge ratios with each other travel on different paths with each other, and are separated spacially (see FIG. 6 described later). On the other hand, said ion detection unit detects ions which come to the predetermined position in the y-direction on said exit plane accordingly. The position of the ion in the y-direction on said exit plane corresponds to the displacement magnitude which occurs during the travel in said separation space.

As above, the mass separation in said mass analyzer is performed based on the difference in the mass-to-charge ratio itself, through the above displacement caused by said one-dimensional high-frequency electric field. The motion of the ion in the extracted direction is not concerned to this displacement. Consequently, this mass separation is in principle less affected by the fluctuation at the initial state of said crude ions before extraction.

In practice, however, the following problem might occur. Said crude ions extracted by said acceleration voltage U have kinetic energies in the extracted direction. These kinetic energies have the standard value $z_i eU$, but are distributed around it with an extent according to the fluctuation at the initial state. Hence, the velocities of the ions in the extracted direction have the standard value $(2z_i eU/m)^{1/2}$ but are distributed around it with an extent. Consequently, the times needed for the ions to arrive at the end of said separation space (the stay times that the ions spend in said separation space) have an extent even among the ions of the same mass-to-charge ratio. If this extent of the stay times brings about some extent of the displacement magnitudes of the ions in the y-direction on said exit plane, the mass resolving power of the spectrometer is restricted by the fluctuation at the initial state as a result.

The present inventor found that the above problem can be solved based on the following fact, and completed the present invention. Since the impulse which acts on an ion from the high-frequency electric field becomes 0 for one period, the rate of the displacement becomes 0 at the time when the ion has received the action for n periods. According to this fact, either of the following two is used in the mass spectrometer of the present invention. One is that said measured ionic species exits from said separation space, when it has received the action of said one-dimensional high-frequency electric field for n periods or for the substantially same time as it after the incidence into said separation space. The other is that said measured ionic species exits from said separation space, after it has received the action of said one-dimensional high-frequency electric field for n periods, within a succeeding off-time in which the electric field strength is 0.

In the former case, we pay attention to the fact that around the time when n periods have passed, there exist a time domain in which the rate of the above displacement is small. In this time domain the extent of the stay times brings about little extent of the displacement magnitudes. Consequently, if all ions of said measured ionic species exsit from said separation space within this time domain, and have received the action of said one-dimensional high-frequency electric field for n periods or for the substantially same time as it, the displacement magnitudes of said measured ionic species on said exit plane are slightly affected by the extent of its stay times.

In the latter case, the displacement becomes in a halting state at the time when n periods have passed, and this halting state is kept throughout the off-time. Hence, the extent of the stay times brings about no extent of the displacement magnitudes. Consequently, if all ions of said measured ionic species exsit from said separation space within the off-time, the displacement magnitudes of said measured ionic species on said exit plane are not affected by the extent of its stay times.

In both case, the mass spectrometer of the present invention is slightly affected by the fluctuation at the initial state, and separates said measured ionic species with higher mass resolution than the case that it is not so. Consequently, it has little necessity to increase the acceleration voltage in order to attain high mass resolution, and the instrument size rarely becomes too large.

In addition, the mass separation of the mass spectrometer of the present invention is not subject to stable periodic motion of ions, such as oscillation and circulation. Consequently, it does not occur that the performance and function are restricted by the conditions and procedures to realize such stable periodic motion. Specifically, in principle this mass spectrometer has no limitation on the mass-to-charge ratio range to be able to deal with. Also it can perform the fast selected ion scan. In this selected ion scan mode, switching of said measured ionic species from one to another is accomplished for n periods of said high-frequency electric field or for a somewhat longer time than it, because said measured ionic species travels through said separation space for n periods, and is distinguished from the other ionic species based on the difference in the displacement magnitude.

The mass separator of the present invention is the same as the mass spectrometer of the present invention, except that said ion detection unit is replaced by said ion selection unit and n is limited to 1, which is the simplest case. The features based on the common constitution are the same as the mass spectrometer. Specifically, it is slightly affected by the fluctuation at the initial state of said crude ions before extraction, and is able to extract said selected ionic species of a predetermined mass-to-charge ratio from said crude ions with high mass resolution. Consequently, it has little necessity to increase the acceleration voltage in order to attain high mass resolution. As a result, the flight length of ions becomes short, and its instrument becomes small and light. In addition, in principle it has no limitation on the mass-to-charge ratio range to be able to deal with, and can also switch said selected ionic species fast from one to another.

BRIEF DESCRIPTION OF DRAWINGS

FIG. 7A-1 is a schematic drawing showing an example of the construction of the ion detection unit shown in FIG. 1, and FIG. 7A-2 is a schematic drawing of a mass spectrum obtained using it;

FIG. 7B-1 is a schematic drawing showing another example of the construction of the ion detection unit shown in FIG. 1, and FIG. 7B-2 is a schematic drawing of a mass spectrum obtained using it;

DESCRIPTION OF EMBODIMENTS

Figure 1:
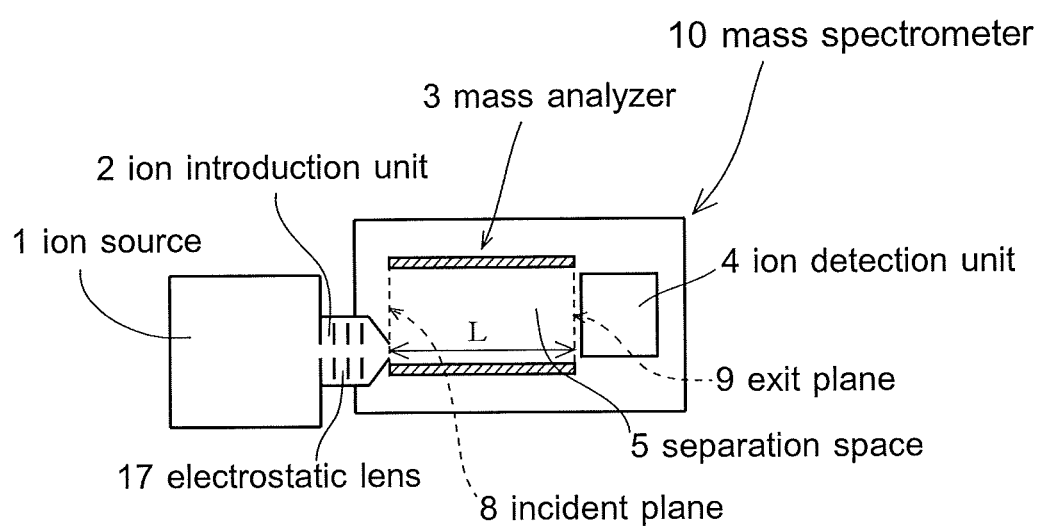
FIG. 1 is a schematic drawing showing the configuration of a mass spectrometer according to embodiment 1 of the present invention.

In a constitution of the mass spectrometer of the present invention, said measured ionic species satisfies the next relation $$T = L(m/2z_i eU)^{1/2},$$

and said crude ions are introduced into said separation space when the strength of said one-dimensional high-frequency electric field is 0, and said measured ionic species exits from said separation space while the electric field strength is substantially 0 one period later. (Here, $z_i$ is the charge number of an ionic species, and m, e, U, L and T are mass of this ionic species, the elementary charge, said acceleration voltage, the effective length of said separation space and the period of said one-dimensional high-frequency electric field, respectively, which are expressed in the SI units. In addition, the effective length of said separation space is the length of the section where said crude ions travel receiving the action of said one-dimensional high-frequency electric field.) The above formula gives the condition which should be satisfied in order that the ions of said measured ionic species having the standard kinetic energy $z_i eU$ in the extracted direction may travel through said effective length of said separation space for one period. The other ions of said measured ionic species travel through said effective length around it. By setting the incident time of said crude ions as above, we can get further advantages that the displacement magnitude for one period becomes maximum and that said measured ionic species is little affected by the fringe field.

In another constitution, said one-dimensional high-frequency electric field has off-times before and after one period, in which the electric field strength is 0, said measured ionic species satisfies the next relation $$T + T_P < T_L < T + T_P + T_O,$$

said crude ions are introduced into said separation space within a former off-time, and said measured ionic species exits from said separation space within a latter off-time. (Here, $T_L$, $T_P$ and $T_O$ are each times needed for ions of said measured ionic species to travel through said effective length of said separation space, a time from the incident time of said crude ions to the beginning of the period, and the length of the latter off-time, which are expressed in the SI units.) In this case all ions of said measured ionic species equally receive the action of said one-dimensional high-frequency electric field for one period. Consequently, the displacement magnitudes are rigorously the same among all ions of the same mass-to-charge ratio. In addition, because multiple ionic species can satisfy the above relation, we can simultaneously analyze the multiple measured ionic species within the mass-to-charge ratio range according to the length of the latter off-time $T_O$.

The above mass spectrometer which uses said one-dimensional high-frequency electric field with said off-times can be a mass spectrometer in which two or more said mass analyzers are placed in series, said crude ions are separated in the first stage mass analyzer at first, part of said measured ionic species separated are detected by said ion detection unit, and the others are introduced into the following mass analyzers to be further separated there and detected by another ion detection unit located in the downstream side. In this case, the others travel between the mass analyzers within said off-time.

The above mass spectrometer which uses said one-dimensional high-frequency electric field with said off-times can also be a mass spectrometer which unites with a time-of-flight (TOF) mass spectrometer, and whose separation space is also part of the drift path of said TOF mass spectrometer, and in which said crude ions are introduced into said separation space and separated in said mass analyzer at first, part of said measured ionic species separated are detected by said ion detection unit, and the others continue traveling on said drift path and are analyzed by said TOF mass spectrometer.

The mass spectrometer of the present invention can be a mass spectrometer in which said mass analyzer has a means to produce in said separation space a x-direction high-frequency electric field whose period is substantially the same as said one-dimensional high-frequency electric field (hereafter referred to as y-direction electric field), and whose phase is different substantially by ¼ period from the y-direction electric field, and which acts in the direction (hereafter referred to as x-direction) crossing the incident direction of said crude ions at a predetermined angle and perpendicular to the y-direction;

said ion detection unit has a means to detect ions which come to the predetermined position in the x-direction on said exit plane;

said crude ions are introduced into said separation space at or immediately before the rising of the y-direction electric field, and said n is one;

another group of crude ions are introduced into said separation space as a pulse at or immediately before the rising of the x-direction electric field, and the measured ionic species of a predetermined mass-to-charge ratio(s) in this group exits from said separation space having received the action of the x-direction electric field for one period or for the substantially same time as it, and is detected in distinction from the other ionic species based on the position in the x-direction on said exit plane.

In the mass spectrometer of the present invention, the waveform of said one-dimensional high-frequency electric field is one of a rectangular wave, a sine wave (equivalent to a cosine wave), a step-wise wave, a trapezoidal wave, a triangular wave, a saw-tooth wave, a waveform in which one of these is partly modified, and a waveform in which two or more of these are composed.

In a scan method of the mass spectrometer of the present invention, the period of said one-dimensional high-frequency electric field is fixed, and said acceleration voltage is changed.

In another scan method, said acceleration voltage is fixed, and the period of said one-dimensional high-frequency electric field is changed.

In the mass spectrometer of the present invention, said ion detection unit may have an ion detector which detects ionic species of mass-to-charge ratios larger than said measured ionic species, together with or separately from the measured ionic species.

Embodiments of the present invention are hereinafter described specifically and in detail with reference to the drawings.

Embodiment 1

In embodiment 1, we describe an example of the mass spectrometer of the present invention which is described in claims 1-3 and 7-10. Here, we describe mainly the usually best case, namely, the case of n=1 that the measured ionic species exits from the separation space having received the action of the one-dimensional high-frequency electric field for one period or for the substantially same time as it. When necessary for description, we use mainly a rectangular wave high-frequency electric field as an example of the one-dimensional high-frequency electric field. We also describe the mass separator of the present invention described in claim 11.

<Overview of the Mass Spectrometer>

FIG. 1 is a schematic drawing showing the configuration of a mass spectrometer 10. The spectrometer 10 consists of an ion source 1, an ion introduction unit 2, a mass analyzer 3, an ion detection unit 4, etc. A passage of ions is in high vacuum at least in the mass analyzer 3 and around it.

The ion source 1 has a means to ionize an analyzed sample and a means to introduce pulsed crude ions into the mass analyzer 3 by a predetermined acceleration voltage. The method of ionization is not limited, and various methods are suitably used according to the purpose of the mass analysis, the quality and state of the analyte and so on. Specifically, these are electron ionization, chemical ionization, field ionization, field desorption ionization, fast atom bombardment ionization, matrix-assisted laser desorption ionization and electrospray ionization and so on. The ion source 1 may be also a collision cell where fragment ions are generated by collision-induced dissociation and so on from precursor ions. In this case, the mass analyzer 3 is, for example, the last stage mass analyzer of a tandem mass spectrometer. The method of making a pulse may be ionizing an analyte in a pulsed manner or extracting in a pulsed manner ions which are generated continuously. The crude ions are introduced into the mass analyzer 3 as a pulse synchronized with the phase of the one-dimensional high-frequency electric field.

The ion introduction unit 2 has a means to focus the flight directions of the crude ions (an electrostatic lens 17 etc.), and/or a means to select out the crude ions which travel toward predetermined directions (a block component having an aperture etc., such as a slit). It is constructed fit for the characteristics of the ion source 1 and the mass analyzer 3.

The mass analyzer 3 has a separation space 5 where the introduced crude ions travel, and a means to produce the one-dimensional high-frequency electric field in the separation space 5. This electric field acts in the direction (y-direction described later) crossing the incident direction of the crude ions, displaces each ion in the y-direction, and makes ionic species having different mass-to-charge ratios with each other travel on different flight paths with each other.

The ion detection unit 4 has an ion detector, and a block component (a slit etc.) located between the exit plane 9 and the ion detector. This block component selectively or semi-selectively allowes ions coming on the predetermined position in the y-direction to pass. The unit 4 has also a signal processing unit etc. which amplifies and stores the output signal from the ion detector. The ion detection unit 4 detects the measured ionic species in distinction from the other ionic species, based on the position in the y-direction on the exit plane 9. This position corresponds to the displacement magnitude which occurs during the travel in the separation space 5.

The feature of the mass spectrometer 10 is that it has the mass analyzer 3 as a mass analyzer and has the ion source 1, ion introduction unit 2 and ion detection unit 4 fit for the mass analyzer 3. We describe these in detail below.

<Structure of the Mass Analyzer>

Figure 2A:
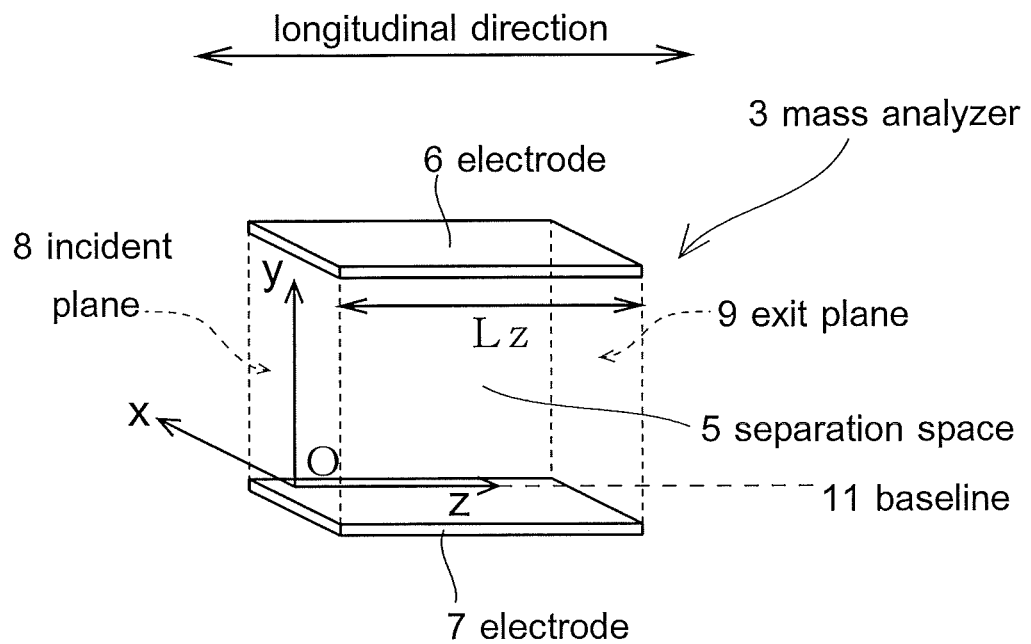
FIG. 2A is a perspective view showing the structure of the mass analyzer shown in FIG. 1.
Figure 2B:
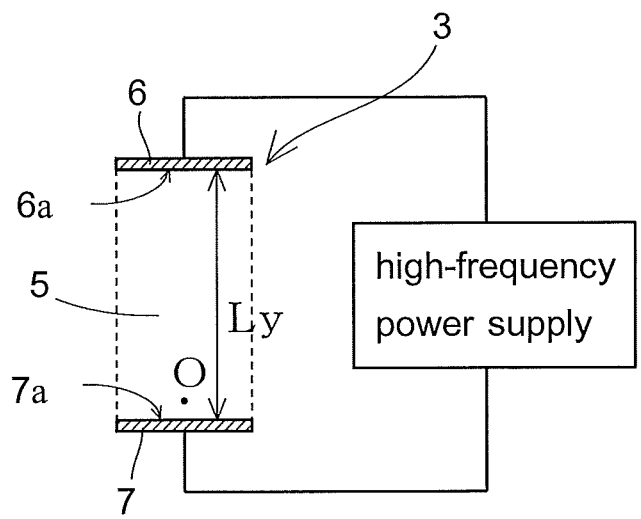
FIG. 2B is a schematic drawing showing the cross-sectional view which cut the above mass analyzer perpendicular to the longitudinal direction.

FIG. 2A is a perspective view showing the structure of the mass analyzer 3, and FIG. 2B is a schematic drawing showing the cross-sectional view which cut the mass analyzer 3 perpendicular to the longitudinal direction. The separation space 5 has a rectangular parallelepiped shape, and two electrodes 6 and 7 are located opposingly at the top and bottom of it. The principal planes 6a and 7a of the electrodes 6 and 7 at the separation space 5 side are flat and mounted parallel to each other. Typically, as shown in FIG. 2, the electrodes 6 and 7 are rectangular plate electrodes of the same length and the same width, and are mounted as their end positions are both aligned with each other in the longitudinal direction and width direction.

Two end planes 8 and 9 of the separation space 5 in the longitudinal direction are used for the incidence and exit of ions, respectively. The incident plane 8 and exit plane 9 are virtual boundary surfaces of the separation space 5 where the one-dimensional high-frequency electric field is produced and the outer space where not. In practice the boundaries of the separation space 5 and the outer space is not surfaces, but domains in which the fringe fields are produced. As described later, in the mass spectrometer 10 we can make the measured ionic species be little or not affected by the fringe fields, by choosing an appropriate phase of the one-dimensional high-frequency electric field at which the crude ions are introduced. In the case that the fringe fields can be neglected and the electrodes 6 and 7 are the above plate electrodes, the plane containing the end faces of these electrodes at the ion source 1 side is the incident plane 8, and the plane containing the end faces at the ion detection unit 4 side is the exit plane 9

Here, for the sake of convenience, we decide a rectangular coordinate system which expresses the position of an ion in the separation space 5, as follows. On the plane which divides the separation space 5 into right and left halves, we draw a straight line parallel to the principal plane 7a in the neighborhood of the electrode 7. We adopt this line as the z-axis, and set the origin O (0, 0, 0) at the intersection of z-axis and the incident plane 8. Then, we take the y-axis from the origin O in the direction which intersects perpendicularly with the principal planes of the electrodes, and take the x-axis in the direction perpendicular to the y- and z-axis. As above decided, the exit plane 9 is the xy-plane at the end of the separation space 5. Furthermore, we call the straight line showing the incident direction of the crude ions the base line 11. Usually but not necessarily, the crude ions are introduced into the separation space 5 at the origin O perpendicular to the incident plane 8. In this case the base line 11 accords with the z-axis.

The effective length L of the separation space 5 is the length of the section where the crude ions travel receiving the action of the one-dimensional high-frequency electric field. This is the length of the base line 11 from the incident position to the intersection with the exit plane 9. In the case that the crude ions are introduced perpendicular to the incident plane 8, and the end of the ion introduction unit 2 is located at the same position as the incident plane 8 in the longitudinal direction as shown in FIG. 1 or located nearer to the ion source 1 than it, the effective length L is the distance between the incident plane 8 and the exit plane 9, namely, the length $L_z$ of the separation space 5. In contrast, in the case that the ions are introduced perpendicular but the end of the ion introduction unit 2 is located into the separation space 5 (not shown in FIG. 1), the effective length L is the distance between the end of the ion introduction unit 2 and the exit plane 9.

<Ion Motion in the One-Dimensional High-Frequency Electric Field>
(One-Dimensional High-Frequency Electric Field)

As shown in FIG. 2B, the electrodes 6 and 7 are electrically connected to a high-frequency power supply, and high-frequency voltage $V_y$ is applied between the electrodes. Then, the electric field $E_y$ given by the next formula $$E_y = -V_y/L_y \quad (1)$$

is produced in the y-direction, where $L_y$ is the distance between the principal planes 6a and 7a of both electrodes. Here, the electrode 7 is kept at the same potential as the end of ion introduction unit 2.

The high-frequency electric field is the AC electric field whose period is equal to or shorter than 2 ms. In the AC electric field, the impulse which acts on an ion from the electric field becomes 0 for one period. Its waveform is arbitrary, but a rectangular wave high-frequency electric field is most preferable. Its advantages are the following (1)-(3).

(1) We can easily and chiefly assemble a small and light high-frequency power supply from a DC constant voltage power supply, wiring applying the output voltage to the electrodes 6 and 7, a switch circuit opening and closing the wiring, and a timer circuit controlling the switch circuit.

(2) The performance of the mass spectrometer is less restricted by the limitation of the high-frequency voltage as a result of the following. We can apply nearly the same voltage as the output voltage of the DC power supply between the electrodes. Consequently, we can apply the exact and high voltage between the electrodes much more efficiently than the case that a high-frequency voltage is created by a high-frequency power supply with an analog circuit such as an oscillation circuit. In addition, the rectangular wave high-frequency electric field can displace ions most effectively, because the electric field strength is kept a constant value (the maximum) throughout each half-period.

(3) We can easily generate exact waveforms having various time intervals with a digital timer circuit. Thus we can easily introduce off-times in which the electric field strength is 0. In addition, since we can widely change the period of the high frequency electric field, we can effectively use the second scan method described later.

Figure 3A:
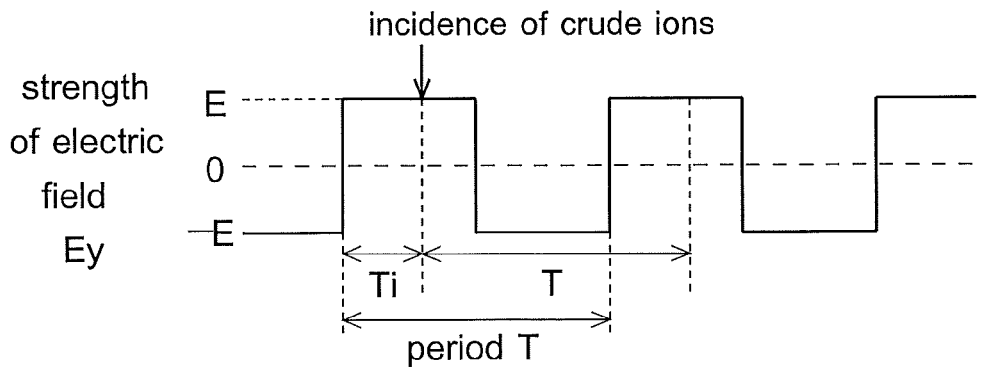
FIG. 3A is a graph showing an example of the rectangular wave high-frequency electric field used in the mass spectrometer shown in FIG. 1.

FIG. 3A is a graph showing a normal rectangular wave high-frequency electric field without off-times. Here, we use symbol T and E which represent the period and strength of the rectangular wave high-frequency electric field, respectively, and set the origin of time t at the rising of the electric field. Then this rectangular wave high-frequency electric field can be given by the next formula $$E_y = E \text{ (in } 0 \le t < T/2),$$

$$E_y = -E \text{ (in } T/2 \le t < T) \quad (2)$$

in $0 \le t < T$, and thereafter these are repeated. In addition, we let the phase of the rectangular wave high-frequency electric field at the incidence of ions be given by incident time Ti measured from the rising of the electric field.

(Ion Motion in the One-Dimensional High-Frequency Electric Field)

Let crude ions be introduced into the separation space 5 at the origin O, and the position of each ion in the separation space 5 be given by coordinates (x, y, z). We use symbols $v_x$, $v_y$ and $v_z$ which represent ion velocity in the x-, y- and z-direction, respectively, and also use symbols $v_{x0}$, $v_{y0}$ and $v_{z0}$ which represent ion velocity at the incidence, respectively. The crude ions are extracted from the ion source 1 by the acceleration voltage U. If we assume that each ion has the kinetic energy $z_i eU$, its velocity v at the incidence is given by the next formula $$v = (2z_i eU/m)^{1/2}. \quad (3)$$

In the case that the crude ions are introduced into the separation space 5 perpendicular to the incident plane 8, we have $$v_{x0}=0;\ v_{y0}=0,$$

$$v_{z0}=v=(2z_i eU/m)^{1/2}. \quad (4)$$

Since there is no electric field in the x-direction in the separation space 5, no displacements occur in the x-direction. Since there is no electric field in the z-direction too, $v_z$ has a constant value $v_{z0}$. Hence, the position in the z-direction of each ion at the time t, when an elapsed time $t-t_0$ has passed from the incidence, is given by the next formula $$z=(2z_i eU/m)^{1/2}(t-t_0), \quad (5)$$

where $t_0$ is the incident time of the crude ions. We call the position given by the equation (5) on the base line 11 the base position, because it would be the position of each ion, supposing the one-dimensional high-frequency electric field does not act. Really, since the electric field acts in the y-direction, each ion is displaced in the y-direction from the base position at the time t, and is on the y-axis perpendicular to the baseline 11 at the base position.

The displacement of ions in the separation space 5, where the one-dimensional high-frequency electric field is produced in the y-direction, is given by the equation of motion $$d^2y/dt^2=dv_y/dt=z_i eE_y/m. \quad (6)$$

Hereafter we discuss the displacement of ions in the y-direction.

By the way, the incident direction of the crude ions has to cross the direction of the electric field, but it is not necessary to be perpendicular to the xy-plane. For example, oblique incidence inevitably occurs when we use an ion source with the orthogonal accelerator. In such a case it is desirable to let the incident direction incline toward the x-direction. Thereby, the next condition $$v_{y0}=0$$

is maintained, and the displacement of each ion in the y-direction is the same as the normal incidence. Consequently, we need not pay special attention to oblique incidence as far as the displacement in the y-direction.

On the other hand, in the case of oblique incidence where the incident direction incline toward the y-direction, the motion of ions is somewhat more complex, because the inertial motion in the incident direction and the displacement caused by the one-dimensional high-frequency electric field have both y-direction components. We describe an example which applies such oblique incidence, later using FIG. 9B.

(Features at the Time when Ions have Received the Action of the One-Dimensional High-Frequency Electric Field for One Period)

The feature (I):

Because the impulse which acts on an ion from the AC electric field becomes 0 for one period, the rate of the displacement in the y-direction $v_y$ returns to the initial velocity $v_{y0}$ at this time. Specifically, it is $$v_y=v_{y0}. \quad (7)$$

Since we now describe about the case of $v_{y0}=0$, we have $$v_y=dy/dt=0.$$

The displacement in the y-direction has halted.
The feature (II):

We use symbol Y which represents the displacement magnitude at the time when an ion has received the action of the one-dimensional high-frequency electric field for one period.

In the case that the electric field is the rectangular wave high-frequency electric field, we substitute formula (2) into equation (6), and integrate twice equation (6) in one period after the incidence of an ion using the initial condition $v_{y0}=0$. Thus we get next formula (8) which gives Y in the rectangular wave high-frequency electric field, $$Y=z_i eET(T-4Ti)/4m \text{ (in } 0 \leq Ti \leq T/2),$$

$$Y=z_i eET(4Ti-3T)/4m \text{ (in } T/2 \leq Ti \leq T). \quad (8)$$

Formula (8) shows that Y changes variously depending on the phase Ti of the rectangular wave high-frequency electric field at the incidence of the ion. According to another point of view, this means that the constant magnitude of Y is obtained, if the ion is introduced into the separation space 5 at a constant phase synchronized with the rectangular wave high-frequency electric field. This displacement magnitude Y is inversely proportional to the mass-to-charge ratio of the ion.

When the one-dimensional high-frequency electric field is another one, the features (I) and (II) are still maintained except that the formula giving Y is different from formula (8).

Figure 3B:
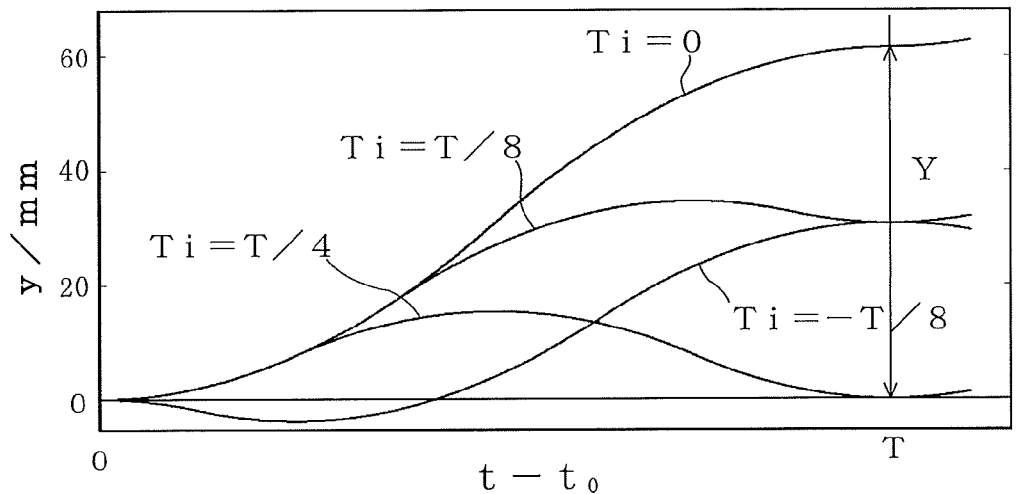
FIG. 3B is a graph which shows the relation between the elapsed time t–t$_0$ and the displacement magnitude y in one period and a little (11 μs) after the incidence of the ion. This figure shows various examples in which the phases of the rectangular wave high-frequency electric field at the incidence are different with each other.

FIG. 3B is a graph which shows the relation between the elapsed time $t-t_0$ and the displacement magnitude y in one period and a little (11 µs) after the incidence of the ion. We calculated the trajectory of the ion by integrating equation (6) numerically with the 5-th order Runge-Kutta method, using the initial condition $v_{y0}=0$. As an example, we calculated about the case that the charge number and mass of the ion are 1 and 100 u (the symbol u stands for the unified atomic mass unit) respectively, and the period T and strength E of the rectangular wave high-frequency electric field are 10 µs and 2546 Vm$^{-1}$ respectively. By the way, we similarly performed all numerical integrations described later with the Runge-Kutta method.

FIG. 3B shows various examples in which the phases Ti of the rectangular wave high-frequency electric field at the incidence of the ion are different with each other. Here, the phases are $-T/8$, 0, $T/8$ and $T/4$, respectively. (When Ti increases (or decreases) by a half-period, the positive/negative of y value becomes reverse, but substantial contents of two cases are the same. Hence, the contents of the case of $3T/8 \leq Ti<7T/8$ are essentially the same as the contents of the case of $-T/8 \leq Ti<3T/8$. Therefore, its illustration is omitted.)

According to formula (8) and FIG. 3B, it is most preferable that Ti is 0 or T/2, because the absolute value of Y becomes maximum. As for 0 or T/2, these cases differ only in that the positive/negative of y values are reverse, and their essential contents are the same. We therefore describe below only the case that Ti is 0. In this case, formula (8) gives $$Y=z_i eET^2/4m. \quad (9)$$

By the way, in the case that Ti is T/4 or 3T/4, Y becomes 0. This is because the displacement to the positive direction and the displacement to the negative direction have canceled out with each other one period later. This relation is used in the mass spectrometer 40 described later in embodiment 4.

FIG. 3B also shows that we have $$v_y=dy/dt=0,$$

when one period has passed as described in the feature (I). Besides, it shows that around this time there exists a time domain in which $v_y$ is quite small.

<Constitution of the Efficient Mass Analyzer>

As described above, each ion introduced into the separation space 5 is displaced in the y-direction by the force received from the one-dimensional high-frequency electric field. The rate of this displacement $v_y$ is inversely proportional to the mass-to-charge ratio of the ion. This displacement in the AC electric field differs from the uniformly accelerated motion in a static electric field. As a result of these, the ionic species having different mass-to-charge ratios with each other travel on different paths with each other, and are separated spacially (see also FIG. 6 described later).

This mass separation is performed based on the difference in the mass-to-charge ratio itself, through the above displacement. The motion of the ion in the extracted direction (z-direction) is not concerned to this displacement. Consequently, this mass separation is less affected by the fluctuation at the initial state in principle, different from the mass separation in the TOF analyzer and magnetic sector analyzer.

In practice, however, the following problem might occur. The ions extracted by the acceleration voltage U have kinetic energies in the extracted direction. These kinetic energies have the standard value $z_i eU$, but are distributed around it with an extent according to the fluctuation at the initial state. Hence, the velocities of the ions in the extracted direction have the standard value $(2z_i eU/m)^{1/2}$, but are distributed around it with an extent. Consequently, the times needed for the ions to arrive at the end of the separation space 5 (the stay times that the ions spend in the separation space 5) have an extent even among the ions of the same mass-to-charge ratio. If this extent of the stay times brings about some extent of the displacement magnitudes of the ions in the y-direction on the exit plane 9, the mass resolving power is restricted by the fluctuation at the initial state as a result.

Paying attention to the above feature (I), the inventor found two methods for solving this problem. The first is to allow the measured ionic species to exit from the separation space 5, when it has received the action of the one-dimensional high-frequency electric field for one period or for the substantially same time as it. The second is to introduce off-times in which the electric field strength is 0, before and after one period. We explain below the first method using a sine wave high-frequency electric field as an example of the one-dimensional high-frequency electric field, and the second method using a rectangular wave high-frequency electric field.

(First Method)

Let the one-dimensional high-frequency electric field be a sine wave high-frequency electric field given by the next formula $$E_y = E_S \sin \omega t, \quad (10)$$

where $\omega$ is the angular frequency of the sine wave high-frequency electric field. We substitute formula (10) into the equation of motion (6), and integrate twice equation (6) in one period after the incidence of an ion using the initial condition $v_{y0} = 0$. Thus we get next formula (11) which gives Y in the sine wave high-frequency electric field, $$Y = (z_i e E_S T^2 / 2\pi m) \cos \omega t_0, \quad (11)$$

where $\omega t_0$ is the phase of the sine wave high-frequency electric field at the incidence of the ion.

It is most preferable that $\omega t_0$ is 0 or $\pi$ as follows. If so, the absolute value of Y becomes maximum according to formula (11). In addition, even if the incident time deviates from the predetermined phase, the change then occurring in Y value is minimized. Furthermore, because the next relation $$E_y = E_S \sin \omega t_0 = 0$$

holds at the incidence, the crude ions are introduced into the separation space 5 when the electric field strength is 0, and the measured ionic species exits from the separation space 5 at the time when the electric field strength becomes 0 one period later or around it. Consequently, the measured ionic species is little affected by the fringe field. As for 0 or $\pi$ these cases differ only in that the positive/negative of y values are reverse, and their essential contents are the same. We therefore describe below only the case that $\omega t_0$ is 0. In this case, formula (11) gives $$Y = z_i e E_S T^2 / 2\pi m. \quad (12)$$

FIG. 4 is a graph which shows the relation between the position z in the z-direction and the displacement magnitude y in one period and a little (11 µs) after the sine wave high-frequency electric field begins to act on ions. This figure shows that by the first method we can almost prevent the mass resolution lowering due to the extent of the stay times.

Figure 4A:
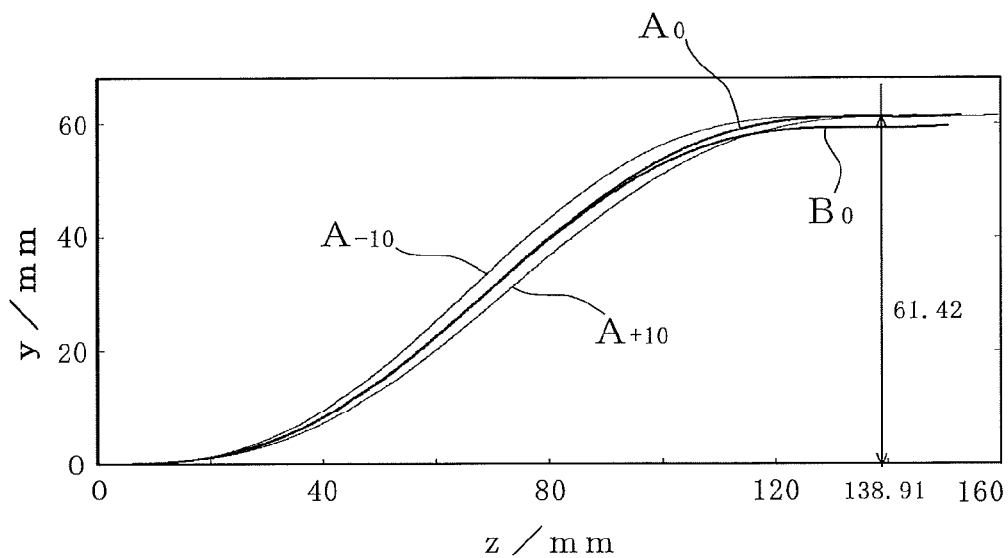
FIG. 4 is a graph which shows the relation between the position z in the z-direction and the displacement magnitude y in one period and a little (11 μs) after the sine-wave high-frequency electric field begins to act on ions in the mass spectrometer shown in FIG. 1.

FIG. 4A shows the results obtained by the numerical integrations of the above equation of motion. We calculated about the case that the charge number and mass of an ionic species A are 1 and 100 u respectively, the same as the case shown in FIG. 3B, the period T and strength Es of the sine wave high-frequency electric field are 10 µs and 4000 Vm$^{-1}$ respectively, and the acceleration voltage U is 100 V. The trajectory $A_0$ (bold line) shows the flight path of ion A traveling with the standard kinetic energy $z_i eU$ in the z-direction. The trajectory $A_{-10}$ and $A_{+10}$ (fine line) show the flight paths of ions A traveling with the 10% smaller and 10% larger kinetic energies than the standard value, respectively. For a comparison, we also calculated about the case that the charge number and mass of an ionic species B are 1 and 103 u (3% larger than the mass of A) respectively, and ion B travels with the standard kinetic energy in the z-direction. The trajectory $B_0$ (bold line) shows this flight path of ion B.

Figure 4B:
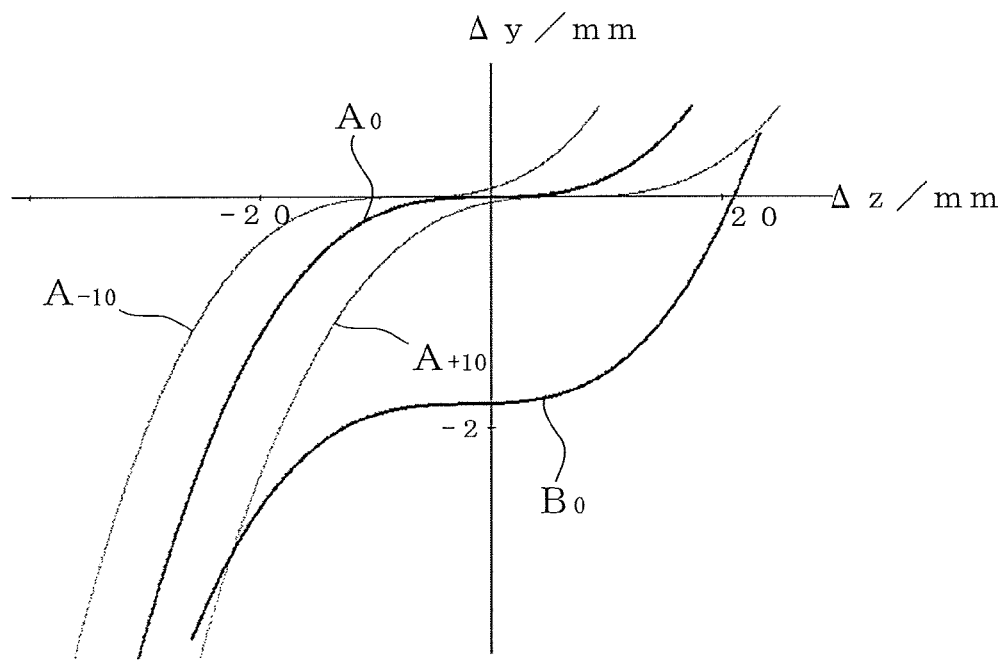

FIG. 4B is an expanded graph. This figure sets the reference point at the point ($z \approx 138.91$ mm, $y \approx 61.42$ mm) on the trajectory $A_0$ one period later, and shows the position in the z-direction and the displacement magnitude by the differences, $\Delta z$ and $\Delta y$, from the reference point, respectively. Here, $\Delta z$ and $\Delta y$ are expanded 2 times and 20 times larger than z and y in FIG. 4A, respectively. The trajectories $A_0$, $A_{-10}$ and $A_{+10}$ are shown in the time range 7.8-11.3 µs from the incidence. Similarly, the trajectory $B_0$ is shown in the time range 8.3-11.9 µs.

It is ideal for the mass analyzer 3 that the crude ions enter into the separation space 5 traveling to the same direction with the same kinetic energy. As described earlier, however, the kinetic energies of the crude ions in the extracted direction have the standard value $z_i eU$, but are distributed around it with an extent according to the fluctuation at the initial state. The trajectories $A_{-10}$ and $A_{+10}$ show examples of the paths on which ions A travel with kinetic energies different from the standard value.

In the case that ions travel with the standard kinetic energy $z_i eU$, their position z is given by formula (5)

$$z = (2z_i eU/m)^{1/2}(t - t_0). \quad (5)$$

In the case that their kinetic energies have the extent, however, the positions z of ions at the same elapsed time $t - t_0$ are not the same with each other even among ions of the same ionic species, but are distributed around the above standard position. The deviations of the trajectories $A_{-10}$ and $A_{+10}$ from the trajectory $A_0$ in the z-direction (the lateral direction of FIG. 4) show examples of the lower and upper limits of this extent, respectively. In other words, it occurs that ions of the same ionic species come on the same position z with the various elapsed times. In this case, the difference in the elapsed times may bring about an extent of the displacement magnitudes y. The deviations of the trajectories $A_{-10}$ and $A_{+10}$ from the trajectory $A_0$ in the y-direction (the vertical direction of FIG. 4) show examples of the upper and lower limits of this extent, respectively.

Because of this extent, for example, if we detect ions B in the region where the trajectory $B_0$ is sandwiched between the trajectories $A_{-10}$ and $A_{+10}$, part of ions A overlap with a major part of ions B and both are not separated. The mass resolution of the spectrometer is restricted by the fluctuation at the initial state as a result.

As shown in FIG. 4, however, at the time when one period has passed after the incidence into the separation space 5 and in a time domain around it, all the trajectories $A_{-10}$, $A_0$ and $A_{+10}$ which show the flight paths of ions A overlap almost into one, and separate completely from the trajectory $B_0$ which shows the standard flight path of ions B. This is because of the following reason. As described as the feature (I), the rate of the displacement $v_y$ is quite small in this time domain, and the next relation $$dy/dt = 0$$

holds substantially. Thereby, even if ions A have come on the same position z with the various elapsed times, this extent of the elapsed times brings about little extent of the displacement magnitudes y, and every displacement magnitude y become almost equal to Y.

Consequently, if all ions of the measured ionic species exsit from the separation space 5 within this time domain, the displacement magnitude of the measured ionic species on the exit plane 9 is little affected by the extent of their stay times. Thereby, the mass separation based on the first method is slightly affected by the fluctuation at the initial state, and the measured ionic species is separated with higher mass resolution than the case that it is not so.

We use the term, the standard ion, to refer to an ion which has the standard kinetic energy $z_i eU$ in the extracted direction among ions of the measured ionic species. We also use symbol $T_L$ which represents times needed for ions of the measured ionic species to travel through the effective length L of the separation space 5, and use symbol $T_{L0}$ which represents $T_L$ of the standard ion. $T_{L0}$ is given by the next formula $$T_{L0} = L/v = L(m/2z_i eU)^{1/2} \quad (13)$$

from formula (3). The standard ions should exit from the separation space 5 one period later, and the other ions of the measured ionic species should exit around it. The condition for this is $$T_{L0} = T. \quad (14)$$

Substituting formula (14) into formula (13), we have the next formula $$T = L(m/2z_i eU)^{1/2}. \quad (15)$$

In the first method we select the acceleration voltage U, the period T of the sine wave high-frequency electric field and the effective length L of the separation space 5, in order that formula (15) may be satisfied for the mass-to-charge ratio of the measured ionic species.

(Second Method)

Figure 3C:
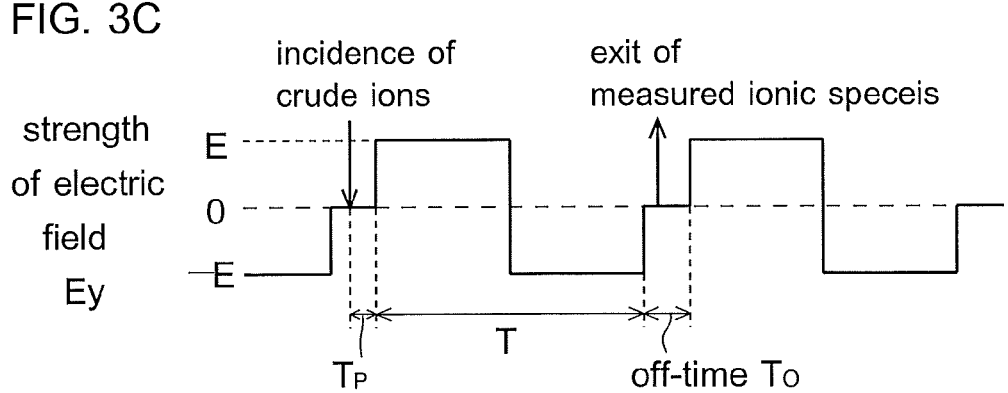
FIG. 3C is a graph showing another example of the rectangular wave high-frequency electric field used in the mass spectrometer shown in FIG. 1.

In the second method, off-times in which the electric field strength is 0 are introduced before and after one period of the rectangular wave high-frequency electric field, as shown in FIG. 3C. The crude ions are introduced into the separation space 5 within a former off-time. The measured ionic species exits from the separation space 5 within a latter off-time, after having received the action of the rectangular wave high-frequency electric field for one period. In this case, because the crude ions receive the action of the electric field from its rising, Y of the measured ionic species is equal to Y in the case of Ti=0 and given by formula (9).

FIG. 5 is a graph which shows the relation between the position z in the z-direction and the displacement magnitude y in one period and a little (11 µs) after the rectangular wave high-frequency electric field with off-times begins to act on ions. This figure shows that by the second method we can completely prevent the mass resolution lowering due to the extent of the stay times.

Figure 5A:
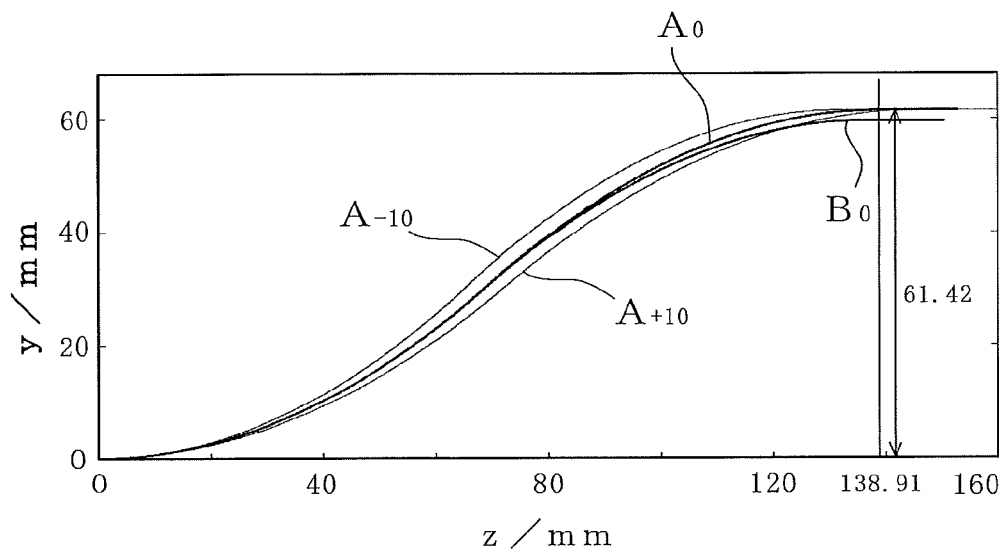
FIG. 5 is a graph which shows the relation between the position z in the z-direction and the displacement magnitude y in one period and a little (11 μs) after the rectangular wave high-frequency electric field with off-times begins to act on ions in the mass spectrometer shown in FIG. 1.

FIG. 5A shows the results obtained by the numerical integrations of the equation of motion (6). We calculated about the case that the charge number and mass of the ionic species A are 1 and 100 u respectively, the same as the case shown in FIG. 4A, the period T and strength E of the rectangular wave high-frequency electric field are 10 µs and 2546 $Vm^{-1}$ respectively, and the acceleration voltage U is 100 V. The explanation about the trajectories $A_0$, $A_{-10}$, $A_{+10}$ and $B_0$ is omitted because it is the same as in FIG. 4A.

Figure 5B:
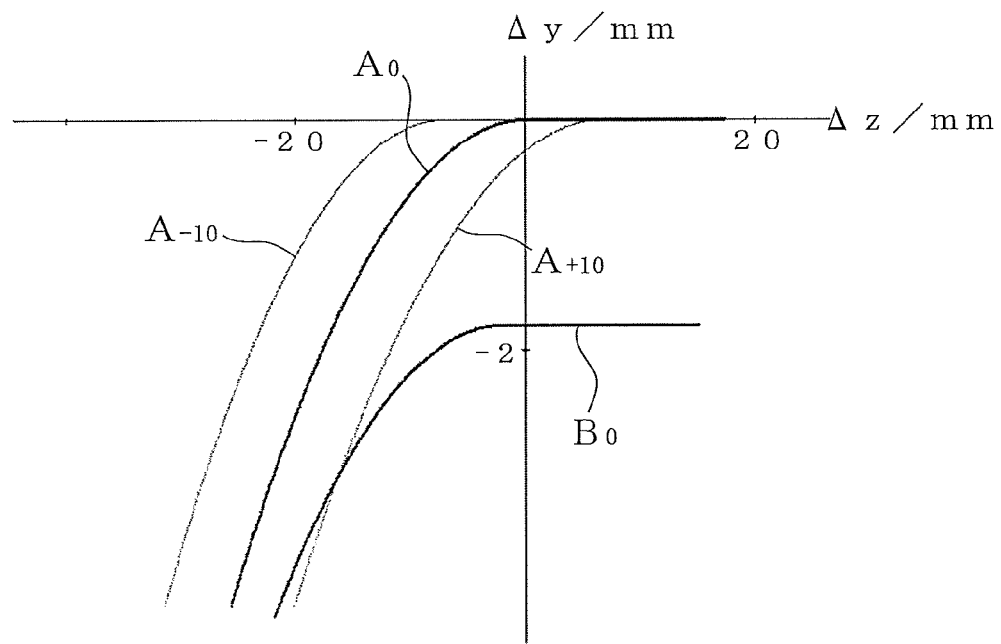

FIG. 5B is an expanded graph similar to FIG. 4B. This figure sets the reference point at the point (z≈138.91 mm, y≈61.42 mm) on the trajectory $A_0$ one period later, and shows the position in the z-direction and the displacement magnitude by the differences, $\Delta z$ and $\Delta y$, from the reference point, respectively. Here, $\Delta z$ and $\Delta y$ are expanded 2 times and 20 times larger than z and y in FIG. 5A, respectively. The trajectories $A_0$, $A_{-10}$ and $A_{+10}$ are shown in the time range 8.2-11.3 µs from the incidence. Similarly, the trajectory $B_0$ is shown in the time range 8.6-11.3 µs.

As shown in FIG. 5B, if the off-time is long enough, all the trajectories $A_{-10}$, $A_0$ and $A_{+10}$ which show the flight paths of ions A overlap completely into one in the off-time one period later, and separate completely from the trajectory $B_0$ which shows the standard flight path of ions B. In addition, this overlapping continues until the end of the off-time. This is because of the following two reasons. Firstly, as long as ions A equally receive the action of the rectangular wave high-frequency electric field for one period, each displacement magnitude Y is given by formula (9), and rigorously the same among all ions A. Secondly, the extent of the stay times in the separation space 5 brings about only an extent of times that ions A spend in the separation space 5 in the off-time. The displacement in the y-direction takes a halting state when one period has passed, and this halting state is kept throughout the off-time. Therefore, the extent of the stay times in the off-time brings about no extent of the displacement magnitudes in the y-direction.

Consequently, even in the case that there is a large fluctuation at the initial state which gives a large extent of the kinetic energies of the measured ionic species in the extracted direction, we can completely prevent any extent of the displacement magnitudes arising from the above extent, merely by introducing off-times long enough accordingly. This is quite noteworthy, because in a TOF mass spectrometer or a magnetic sector mass spectrometer, a large acceleration voltage is needed to attain high mass resolution, and a special design such as a reflectron TOF mass spectrometer or a double-focusing sector mass spectrometer is needed to attain higher mass resolution.

In addition, the measured ionic species is not affected by the fringe field, because the crude ions are introduced into the separation space 5 within the off-time, and the measured ionic species exits from the separation space 5 within the off-time. Moreover, since the measured ionic species travel in parallel to the base line 11 after exiting, the flexibility increases remarkably about the positions where a slit and an ion detector are located in the z-direction.

(Comparison of the First and Second Method)

According to the first or second method, the mass spectrometer 10 is slightly affected by the fluctuation at the initial state. Consequently, it has little necessity to increase the acceleration voltage in order to attain high mass resolution, and its instrument size rarely becomes too large. As shown in FIG. 4B, however, the trajectories $A_{-10}$, $A_0$ and $A_{+10}$ do not completely overlap into one in the first method, and this restricts mass resolution. Furthermore, in the case that the one-dimensional high-frequency electric field is a rectangular wave electric field, the first method is not as effective as in the case that it is a sine wave electric field. This is because in the rectangular wave electric field its strength changes instantaneously at the rising and falling and there is no time domain where its strength is near 0.

Therefore, we describe hereafter only the case that we use the second method and the one-dimensional high-frequency electric field is a rectangular wave high-frequency electric field. By the way, the same effect is obtained by introducing off-times to the one-dimensional high-frequency electric field, even if it is one other than the rectangular wave electric field, for example, a sine wave electric field. But an electronic circuit to realize this becomes complex. Consequently, the rectangular wave high-frequency electric field is most preferable for the one-dimensional high-frequency electric field with off-times.

(Condition which the Measured Ionic Species should Satisfy)

As described in the section (First Method), we use symbol $T_L$ which represents the time needed for the measured ionic species to travel through the effective length L of the separation space 5, and also use symbol $T_{L0}$ which represents $T_L$ of the standard ion. The ions of the measured ionic species introduced within the off-time should exit from the separation space 5 within the off-time one period later. The condition for this is $$T+T_P<T_L<T+T_P+T_O, \quad (16)$$

from FIG. 3C, where $T_P$ is a time from the incident time of the crude ions to the beginning of the period, and $T_O$ is the length of the off-time one period later. Here, we do not include the length of the off-time $T_O$ in the period T in the present Description.

When $T_L$ has an extent $\pm T_E$ due to the fluctuation at the initial state, formula (16) gives $$T+T_P+T_E<T_{L0}<T+T_P-T_E+T_O. \quad (17)$$

Substituting formula (13) into formula (17), we have the next formula $$T+T_P+T_E<L(m/2z_ieU)^{1/2}<T+T_P-T_E+T_O. \quad (18)$$

We use symbol $T_D$ which represents the duration of the pulsed crude ions. In the case that ions are generated in a pulsed manner, $T_D$ is usually short. If $T_D$ is negligible in comparison to T, we can assume that $T_P$ has no time width, and $T_0$ is long enough if it is longer than $2T_E$ according to formula (17). In contrast, in the case that ions are generated continuously and the crude ions are introduced as a pulse whose duration is unnegligible in comparison to T, $T_P$ has a time width same as $T_D$. In this case $T_0$ should be longer than $T_D+2T_E$.

In principle the length of $T_D$ is arbitrary. But, if $T_D$ becomes long, L needs to be lengthened accordingly. Its length therefore has a practical limit. On the other hand, if $T_D$ becomes short, the amount of ions introduced in one pulse of crude ions decreases accordingly. Consequently, it is necessary to decide an appropriate length of $T_D$ taking both into consideration.

There is no limitation for $T_P$, except that $T_P$ is positive at the end of the pulsed crude ions. If $T_P$ is somewhat longer than the above minimum, it brings about a merit that even if the incident time of the pulsed crude ions deviates from the predetermined time, no problem occurs in the case that the deviation is within this additional length. If $T_P$ becomes longer, however, L needs to be lengthened accordingly.

$T_P$ and $T_0$ should be minimums respectively, in order that the mass spectrometer 10 may not be enlarged uselessly and can operate efficiently in terms of time. Specifically, $T_P$ and $T_0$ should satisfy the next relation $$T_P \approx 0-T_D, \quad (19)$$

$$T_0 \approx T_D+2T_E, \quad (20)$$

respectively, and should be somewhat larger than the right side. In this time the following two conditions become almost the same. One is the condition which enables the ions having the shortest stay time among the ions of the measured ionic species introduced at the front end of the pulsed crude ions to exit from the separation space 5 immediately after the beginning of the off-time. The other is the condition which enables the ions having the longest stay time among the ions of the measured ionic species introduced at the rear end of the pulsed crude ions to exit from the separation space 5 immediately before the ending of the off-time. These conditions are that $T_{L0}$ satisfies the next formula $$T_{L0}=L(m/2z_ieU)^{1/2} \approx T+T_D+T_E, \quad (21)$$

and is somewhat larger than the most right side.

In the second method we select the acceleration voltage U, the period T of the one-dimensional high-frequency electric field and the effective length L of the separation space 5, in order that formula (18), or more specifically, for example, formula (21) may be satisfied for the mass-to-charge ratio of the measured ionic species. If U and T are the same respectively, L which satisfies formula (18) is longer than L which satisfies formula (15), as much as $T_D+T_E$ is added to T. Similarly, if L and T are the same respectively, U which satisfies formula (18) is smaller than U which satisfies formula (15).

(Condition which Enables the Measured Ionic Species to be Detected)

The ion detection unit 4 is constructed to detect ions which come to the position apart from the intersection (0,0) of the baseline 11 and the exit plane 9 by a distance C in the y-direction on that plane (see also the section <Ion Detection Unit> described later). On the other hand, the ions of the measured ionic species come on the exit plane 9 receiving the action from the one-dimensional high-frequency electric field for one period. The high-frequency electric field meanwhile displaces these ions by the magnitude Y in the y-direction. Hence, if the next relation $$C=Y \quad (22)$$

is satisfied, the measured ionic species can be detected in distinction from the other ionic species, based on the position in the y-direction on the exit plane 9.

In the case that the one-dimensional high-frequency electric field is the rectangular wave high-frequency electric field, we have $$C=z_ieET^2/4m \quad (23)$$

from formulas (22) and (9). In the mass spectrometer 10, we select the period T and strength E of the rectangular wave high-frequency electric field, in order that formula (23) may be satisfied for the mass-to-charge ratio of the measured ionic species. E which satisfies formula (23) is proportional to the mass-to-charge ratio of the measured ionic species, if T is fixed.

So far, we have described about the case of n=1, in which the measured ionic species exits from the separation space 5, having received the action of the one-dimensional high-frequency electric field for one period or for the substantially same time as it. Letting m be a natural number larger than one, however, the feature (I) and (II) described earlier are satisfied at the time of $t=t_0+mT$, when an ion has received the action of the high-frequency electric field for m periods. In the mass spectrometer 10, therefore, we can get the similar effects as the case of n=1, even if the period is shortened by a factor of 1/m, and the measured ionic species exits from the separation space 5, having received the action of the one-dimensional high-frequency electric field for m periods or for the substantially same time as it.

However, for example, in the case of n=2, in which the period is a half of the stay time in the high-frequency electric field, the displacement magnitude for one period Y becomes ¼ times smaller than the case of n=1 (see formula (9)). Consequently, if the stay time in the high-frequency electric field is the same, the displacement magnitude in the stay time becomes ½ times smaller than the case of n=1. In this way, the displacement magnitude in the same stay time becomes maximum in the case of n=1. We should therefore select one as n, if we have no specific reason to avoid it.

<Scan>

In the scan mode, the mass spectrometer 10 detects plural ionic species of different mass-to-charge ratios as the measured ionic species in time-series. The scan has two mode. In the normal scan mode, the spectrometer 10 scans an predetermined mass-to-charge ratio range continuously, and detects all ionic species within this range in order of the mass-to-charge ratio to yield a mass spectrum. In the selected ion (switching over ion) scan mode, the spectrometer 10 switches over and selectively detects some ionic species of different mass-to-charge ratios one after another. In the selected ion scan mode respective amounts of some ionic species of specific mass-to-charge ratios can be measured repeatedly in a short time.

In the mass spectrometer 10, the effective length L of the separation space 5 is fixed in scanning. For given L, therefore, the acceleration voltage U or the period T of the rectangular wave high-frequency electric field is changed, in order that formula (16) or (18), or more specifically, for example, formula (21) may be satisfied for the change of the mass-to-charge ratio of the measured ionic species. Furthermore, combination of these two changes enables a wider range of the mass-to-charge ratio be scanned than each change alone.

(First Scan Method)

In the first scan method, the period T is fixed, and the acceleration voltage U is changed according to the mass-to-charge ratio of each measured ionic species to be detected, in order that they may sequentially satisfy formula (16) or (18). More specifically, for example, U is changed proportional to their mass-to-charge ratios in order that their $T_{LO}$ may sequentially become a predetermined constant value. Thereby, if formula (21) is satisfied at the beginning of the scan and $T_E$ does not much increase subsequently, they sequentially satisfy formula (21) automatically in scanning. Consequently the operation of the spectrometer 10 becomes simple.

Because in the normal scan mode plural ionic species are usually detected by one ion detector in time-series, the distance C is constant. In this case the strength E of the rectangular wave high-frequency electric field is also changed proportional to their mass-to-charge ratios, in order that each measured ionic species may sequentially satisfy formula (23) in the progress of scanning.

In the above scan method, U and E are proportional to the mass-to-charge ratio. Hence, we can easily determine the mass-to-charge ratio of the measured ionic species from the peak position in the mass spectrum. When a too wide range of the mass-to-charge ratio is scanned, it may occur that part of values of U or E become too small or too large by the scan with a single value of T. In this case, the mass-to-charge ratio range is divided into two or more ranges, and a smaller mass-to-charge ratio range is scanned with a short T fixed, whereas a larger mass-to-charge ratio range with a long T fixed.

In the selected ion scan mode also, in the case that plural ionic species are detected by one ion detector in time-series, U and E are changed proportional to the mass-to-charge ratio of each measured ionic species to be detected, similarly to in the normal scan mode. In contrast, the spectrometer 10 may have two or more ion detectors which detect ions coming on the different positions in the y-direction respectively, and may detect plural ionic species by individual ion detectors for each ionic species. In this case E is fixed and only U is changed.

In both case, switching of the measured ionic species from one to another is accomplished for one period of the rectangular wave high-frequency electric field or for a somewhat longer time than it, for example, 10 µs and a little, because the measured ionic species travels through the separation space 5 for one period, and it is distinguished from the other ionic species based on the difference in the displacement magnitude. Thereby the spectrometer 10 can repeatedly measure respective amounts of plural ionic species in a short time.

(Second Scan Method)

In the second scan method, U is fixed and T is changed according to the mass-to-charge ratio of each measured ionic species to be detected. The spectrometer 10 detects each ionic spesies which satisfies formula (16) sequentially, as the measured ionic species. More specifically, for example, T is changed in order that the square $T^2$ of the period may be proportional to the mass-to-charge ratio of each measured ionic species. In this case, since U is fixed, $T_{LO}$ of each ionic species is unchanged. If T is changed on this condition, $T_{LO}$ which satisfies formula (17) changes for each T. Consequently, the ionic species having corresponding values of $T_{LO}$ are detected sequentially as the measured ionic species which satisfies formula (18).

Since plural ionic species are usually detected by one ion detector in time-series, E is also fixed. When a too wide range of the mass-to-charge ratio is scanned, it may occur that part of values of T become too small or too large by the scan with a single values of U and E. In this case, the mass-to-charge ratio range is divided into two or more ranges, and a smaller mass-to-charge ratio range is scanned with a small U and E fixed, whereas a larger mass-to-charge ratio range with a large U and E fixed. These are the same both in the normal scan mode and in the selected ion scan mode.

In this case, it is preferable that the length of the off-time $T_O$ is changed proportional to T from the following reasons. As described earlier, the effective length L of the separation space 5 needs to be lengthened according to the length of $T_D$. The increase of L is principally decided by the ratio of $T_D$ to T, $T_D/T$. In order to use the effective length L most efficiently, therefore, $T_D$ should be proportional to T in order that $T_D/T$ may keep the most suitable constant value. Moreover, it is supposed that $T_E$ is nearly proportional to $T_{LO}$, and eventually to T. If $T_O$ satisfy formula (20), therefore, it is natural to let $T_O$ be proportional to T. Thereby, if formula (21) is satisfied at the beginning of the scan, each measured ionic species sequentially satisfies formula (21) automatically in scanning. Consequently the operation of the spectrometer 10 becomes simple.

(Example of the Scan)

Figure 6A:
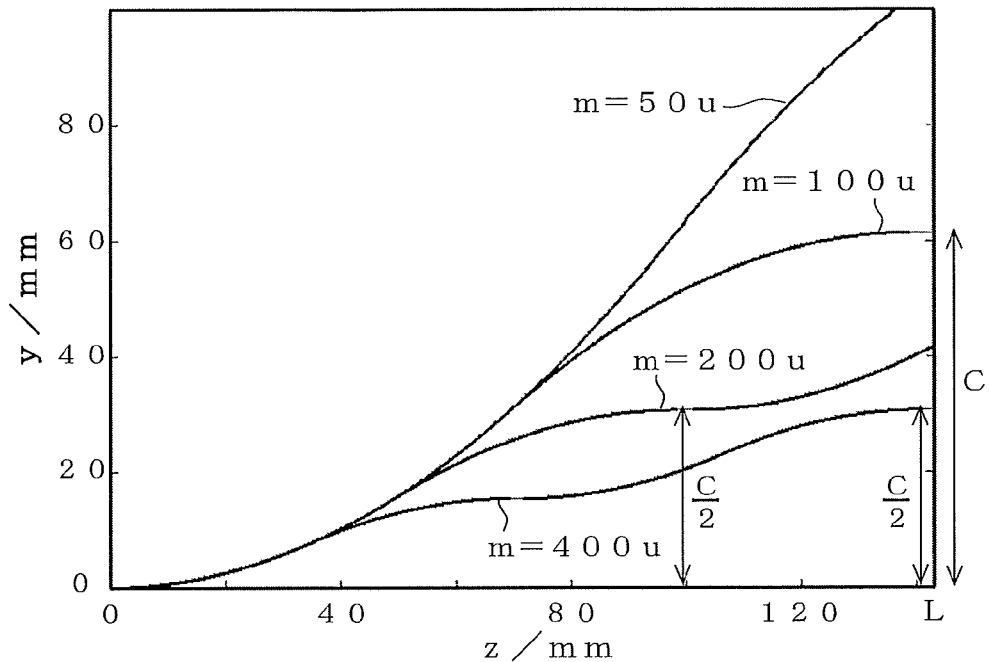
FIG. 6A is a graph which shows trajectories of various ionic species in the mass spectrometer shown in FIG. 1.
Figure 6B:
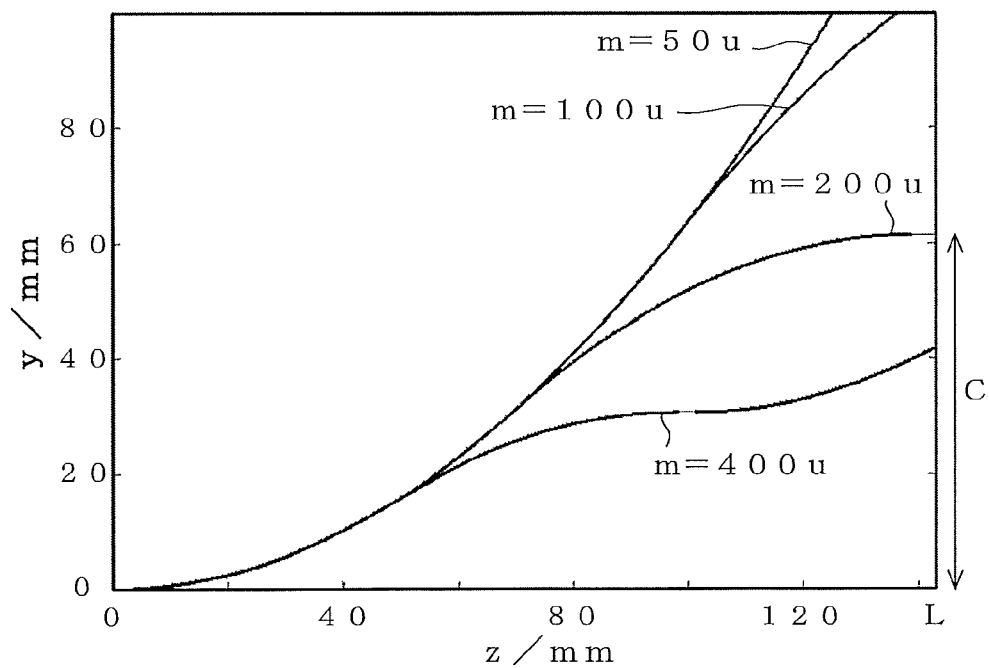
FIG. 6B is a graph which shows trajectories after scanning by the first scan method.

FIG. 6A is a graph which shows trajectories of various ionic species in the mass spectrometer 10. FIG. 6B is a graph which shows trajectories after scanning by the first scan method. FIGS. 6A and 6B show the results obtained by the numerical integrations of the equation of motion (6). We calculated about the case that the charge numbers of ionic species are 1, their masses are 50 u, 100 u, 200 u and 400 u respectively, and the period T of the rectangular wave high-frequency electric field is 10 μs. The trajectories show the flight paths of ions traveling with the standard kinetic energy $z_i eU$ in the z-direction. The bold lines show the flight paths in the high-frequency electric field, whereas the short fine lines the flight paths in the off-time.

Here, we make $T_P$ and $T_0$ a minimum length respectively. If we substitute above m and T, and U below into formula (15), we obtain 138.9 mm as the length which satisfies formula (15). According to the fluctuation at the initial state, we make the effective length L of the separation space 5 somewhat longer than it, in order that all ions of the measured ionic species may stay in the separation space 5 at least for one period. The ion detection unit 4 is constructed to detect ions which come to the position apart from the intersection (0,0) of the baseline 11 and the exit plane 9 by the distance C=61.42 mm in the y-direction on the plane 9.

FIG. 6A shows the trajectories in the case that the acceleration voltage U is 100 V and the strength E of the rectangular wave high-frequency electric field is 2546 $Vm^{-1}$. In this case, it is known from formula (5) that the standard ion of the ionic species of mass 100 u travels 138.9 mm toward the z-direction for one period. Then this ion travels somewhat toward the z-direction in the off-time and arrives at the exit plane 9. That is to say, the ionic species of mass 100 u exits from the separation space 5 as the measured ionic species within the off-time after having received the action of the high-frequency electric field for one period. At this time the displacement magnitude Y is 61.42 mm, which is equal to C. Unlike it, ionic species of mass smaller than 100 u, for example 50 u, arrives at the exit plane 9 before receiving the action of the high-frequency electric field for one period, and the displacement magnitude y is larger than C (or the displacement magnitude y becomes so large that the ions hit the electrode 6 and do not arrive at the exit plane 9). In contrast, ionic species of mass larger than 100 u, for example 200 u or 400 u, arrives at the exit plane 9 after receiving the action of the high-frequency electric field for a longer time than one period and the displacement magnitude y is smaller than C. Thereby, only the measured ionic species of mass 100 u is detected by the ion detection unit 4. By the way, the displacement magnitude Y of the ionic species of mass 200 u for one period is C/2. The ionic species of mass 400 u needs 20 μs (two periods) and a little to travel through the separation space 5 and the displacement magnitude y at the exit plane 9 is C/2.

On the other hand, FIG. 6B shows the trajectories in the case that U is 200 V and E is 5092 $Vm^{-1}$. In this case, since U doubles, the ion velocity $v_{z0}$ in the z-direction becomes $2^{1/2}$ times larger (see formula (4)) for all ionic species, which arrive at the exit plane 9 more quickly than the trajectories shown in FIG. 6A. As a result of this, the ionic species of mass 100 u exits the separation space 5 before receiving the action of the high-frequency electric field for one period. In place of it, the ionic species of mass 200 u, whose mass is 2 times larger and thus the ion velocity $v_{z0}$ is $(½)^{1/2}$ times smaller than it, exits from the separation space 5 as the measured ionic species within the off-time after having received the action of the high-frequency electric field for one period. Since E doubles also, the displacement magnitude Y for one period becomes 2 times larger (see formula (9)). As a result of this, the displacement magnitude Y of the ionic species of mass 200 u becomes equal to C. Unlike this, the displacement magnitude y of the ionic species of mass 100 u at the exit plane 9 is larger than C. In contrast, the displacement magnitude y of the ionic species of mass 400 u at the exit plane 9 is smaller than C. Thereby, only the measured ionic species of mass 200 u is detected by the ion detection unit 4.

Comparing FIG. 6A with FIG. 6B, we know that the trajectory of the ionic species of mass 100 u in FIG. 6A is the same as the trajectory of the ionic species of mass 200 u in FIG. 6B. This holds true regardless of the scan method. If L and C are the same respectively, the measured ionic species travels on the same flight path and is detected in the mass spectrometer 10.

<Ion Source and Ion Introduction Unit>

The ion source 1 may be a usual ion source or an ion source with the orthogonal accelerator. In the latter case, the positions of ions of a given ionic species coming on the exit plane 9 expand linearly in one direction. Letting this direction be the x-direction, we can use it without lowering the mass resolution in the y-direction. In the case that the ion source ionizes an analyte continuously in terms of time, the ion availability improves with an ion source with the orthogonal accelerator, because part of ions generated between intermittent extraction periods can be used. Here, we define and use the term, ion availability, as ratio of the amount of ions detected in the ion detection unit 4 to the amount of ions of the measured ionic species generated in the ion source 1.

The ion introduction unit 2 has a focusing means such as the electrostatic lens 17. In the mass spectrometer 10, the ionic species separated spacially in the separation space 5 are selected out by the ion detection unit 4 based on the position in the y-direction on the exit plane 9. The electrostatic lens 17 should therefore be designed as the measured ionic species is best focused on the ion detection unit 4. The higher the performance of the electrostatic lens 17 is, the higher the ion transmittance and the mass resolution are. Hence the electrostatic lens 17 is a very important component of the mass spectrometer 10.

FIG. 1 shows an example that the ion introduction unit 2 is located on the down-stream side of the ion source 1, but their arrangement is not restricted to this. The distinction between the ion source 1 and the ion introduction unit 2 is notional and functional, and is not the classification on arrangement. Both are actually unified and located in many cases. For example, an electrostatic lens is built into an ion source with the orthogonal accelerator to give convergency to the ion beam before the orthogonal acceleration.

<Ion Detection Unit>

Figures 1, 7A:
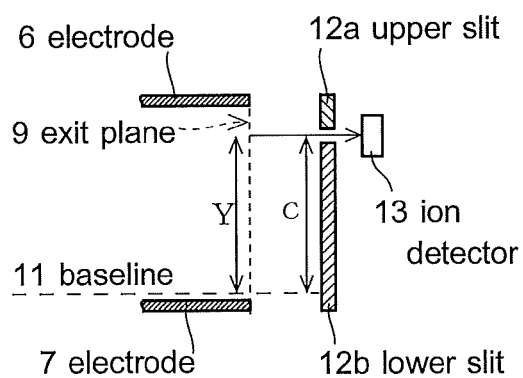
Figures 2, 7A:
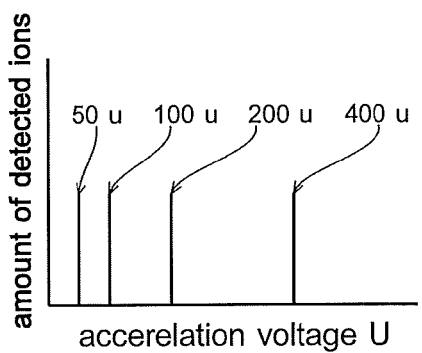

FIG. 7A-1 is a schematic drawing showing an example of the construction of the ion detection unit 4. This ion detection unit has an ion detector 13 and a slit 12 located between the exit plane 9 and the ion detector 13. The slit 12 is an example of the block component which selectively allowes the measured ionic species to pass. The center line of the aperture between the upper slit 12a and lower slit 12b is located at the position apart from the baseline 11 by the distance C in the y-direction. The size of the aperture is variable and is selected according to required mass resolving power and so on. It is, for example, about 0.05-0.5 mm By using the slit 12, the mass spectrometer 10 can perform both high sensitivity measurement and high resolution measurement. The former gives priority to the transmittance of the measured ionic species, holding mass resolution comparatively low. Whereas, the latter provides high mass resolution, although the transmittance is lowered.

The ion detector 13 should be able to detect ions coming through the slit 12. If only so, an appropriate one can be chosen according to the design of the ion detection unit 4. If the ions come only on the y-axis, the ion detector 13 may be one having a narrow ion detection area. This is, for example, a secondary electron multiplier, a channel electron multipliers, a Faraday cup, etc. each of which has a small aperture. In contrast, if the ions come on with an extent in the x-direction, the ion detector 13 should be one having an ion detection area corresponding to this extent. Accordingly, the ion detector 13 should be one which has an aperture of appropriate size, among secondary electron multipliers, channel electron multipliers, microchannel plates, Faraday cups, etc. In each case a postacceleration detector or a conversion dynode detector can be used to stabilize detection sensitivity.

FIG. 7A-2 is a schematic drawing of a mass spectrum which is obtained when the measured ionic species shown in FIG. 6 are scanned by the first scan method using this ion detection unit. In this case, these species are scanned in order of their mass-to-charge ratios according as the increase in the acceleration voltage U and strength E of the rectangular wave high-frequency electric field, and the peaks of the amount of detected ions are observed reflecting their abundances. At this time, since the mass-to-charge ratio is proportional to U and E, their mass-to-charge ratios are easily determined from the peak positions in the mass spectrum.

Figures 1, 7B:
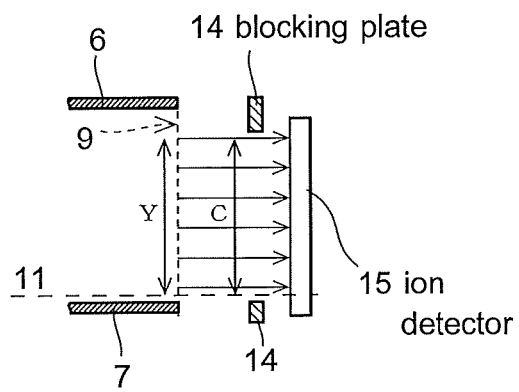
Figures 2, 7B:
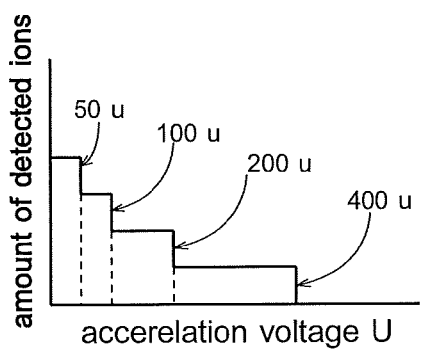

FIG. 7B-1 is a schematic drawing showing another example of the construction of the ion detection unit 4. This ion detection unit has an ion detector 15 and a blocking plate 14 located between the exit plane 9 and the ion detector 15. The blocking plate 14 is an example of the block component which semi-selectively allowes the measured ionic species to pass. That is to say, the blocking plate 14 allowes the measured ionic species and ionic species of mass-to-charge ratios larger than it to pass, but does not allow ionic species of the mass-to-charge ratio smaller than it to pass.

FIG. 7B-2 is a schematic drawing of a mass spectrum which is obtained when the above measured ionic species are scanned by the first scan method using this ion detection unit. In this case, while U and E are small, all these ionic species pass through the blocking plate 14 and are detected by the ion detector 15. Then, according as the increase in U and E, these species are prevented to pass through the blocking plate 14 in order of their mass-to-charge ratios, and are eliminated from the ionic species detected by the ion detector 15. Consequently, the stairs-shaped spectrum is obtained as shown in FIG. 7B-2. In this spectrum, the positions where the amount of detected ions decreases suddenly are the positions where the peaks are observed in the usual mass spectrum.

This ion detection unit have the following features.

(1) It measures the amount of all ionic species or the measured ionic species and ionic species of mass-to-charge ratios larger than it, among ionic species extracted from the ion source 1. Consequently, it does not overlook high mass ionic species, and can judge easily and accurately when the scanning should be closed.

(2) An amount of a given measured ionic species can be known directly from the difference in the signal intensity before and after the position where this species is eliminated from the ionic species detected. In order to get this amount in the usual mass spectrum, we must integrate the peak to get the peak area. The present method is simpler and more accurate than the usual method and can thereby simplify a data handling system.

(3) If the usual mass spectrum is necessary, it can be obtained by differenciating the stairs-shaped spectrum. The differenciation of the spectrum is easier than the integration.

The ion detector 15 should be able to detect ions coming through the blocking plate 14. If only so, an appropriate one can be chosen according to the design of the ion detection unit 4. However, in order for this ion detection unit to make full use of the above features, the ion detector 15 should have high linearity, namely, performance to generate an output signal proportional to the amount of ions for a wide range of their amount. In addition, since the ions come on a long line- or belt-shaped domain, the ion detector 15 should have a long ion detection area corresponding to this domain, if it detects the ions just as they come. Accordingly, the ion detector 15 should be one having a long ion detection area, among secondary electron multipliers, channel electron multipliers, microchannel plates, Faraday cups, etc. Whereas, if it detects the ions after letting them converge in an electrostatic field and so on, an ion detector having a shorter ion detection area can be used.

Figure 7C:
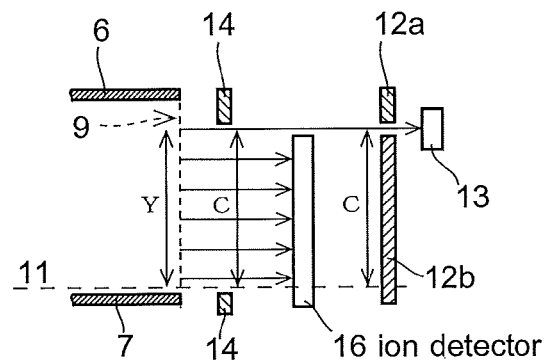
FIG. 7C is a schematic drawing showing yet another example of the construction of the ion detection unit shown in FIG. 1.

FIG. 7C is a schematic drawing showing yet another example of the construction of the ion detection unit 4. This ion detection unit has the slit 12 and ion detector 13, and also has the blocking plate 14 and an ion detector 16. FIG. 7C shows these locations in the z-direction.

As already described, the slit 12 and ion detector 13 detect the measured ionic species according to high sensitivity measurement and high resolution measurement respectively. In addition, a major part of ionic species of mass-to-charge ratios larger than the measured ionic species are detected by the ion detector 16. When the above measured ionic species are scanned by the first scan method using this ion detection unit, the mass spectrum shown in FIG. 7A-2 is obtained from the ion detector 13 and a mass spectrum almost the same as FIG. 7B-2 is obtained from the ion detector 16.

Consequently, by using this ion detection unit, the mass spectrometer 10 scans monitoring the amount of all ionic species or ionic species of mass-to-charge ratios larger than the measured ionic species, among ionic species extracted from the ion source 1. As a result, it does not overlook high mass ionic species, and can judge easily and accurately when the scanning should be closed. Besides, because it can use a sensitive ion detector for the ion detector 13, it can measure the measured ionic species with high sensitivity. In contrast, since the ion detection unit shown in FIG. 7B-1 has only one ion detector 15 as an ion detector, it might be difficult to reconcile high sensitivity measurement of the measured ionic species and measurement of many ionic species.

The ion detector 16 may be one similar to the ion detector 15. If it is merely used as a monitor, however, the detector 16 needs not have so high linearity as the detector 15 should have. Hence there is a wider choice for the detector 16. The ion detector 16 also can be used as follows, different from the ion detector 15. Several anodes are prepared with patterning on the backside of a microchannel plate used as the ion detector 16. By these anodes, the ion detection area of the microchannel plate is divided to several regions according as the difference in the position in the y-direction, and the amount of ionic species coming on each region is measured individually. Thereby, the amounts of ionic species of mass-to-charge ratios larger than the measured ionic species can be measured in connection with the positions in the y-direction, and information can be obtained about not only their abundances but also their mass-to-charge ratio ranges.

<Simultaneous Analysis of Multiple Measured Ionic Species>

Multiple ionic species may satisfy formula (18). Hence, using the rectangular wave high-frequency electric field with the off-times, the mass spectrometer 10 can simultaneously analyze the multiple measured ionic species within the mass-to-charge ratio range corresponding to the length of the off-time $T_O$.

Figure 8A:
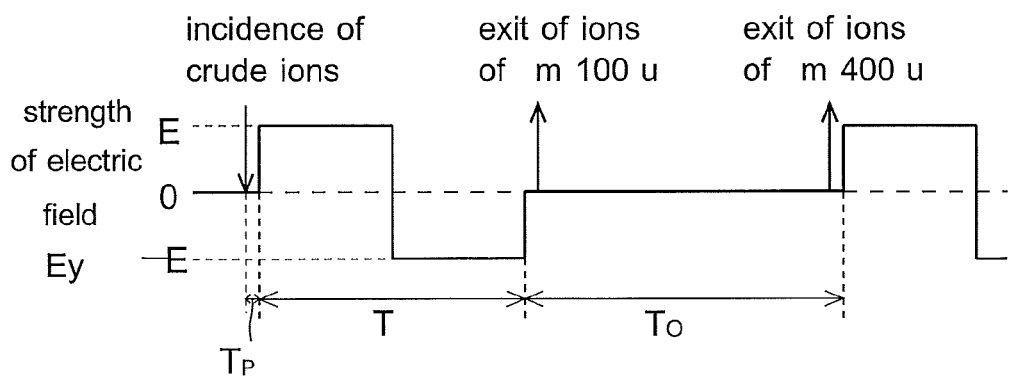
FIG. 8A is a graph showing an example of the rectangular wave high-frequency electric field which is used simultaneously to analyze the multiple measured ionic species in the mass spectrometer shown in FIG. 1.

FIG. 8A is a graph showing an example of the rectangular wave high-frequency electric field which is used to analyze simultaneously the multiple measured ionic species of the charge numbers 1 and masses 100-400 u. The crude ions are introduced into the separation space 5 immediately before the rising of the high-frequency electric field. The incident time may be anytime within the off-time. But, if it is immediately before the rising, the effective length L of the separation space 5 is used most efficiently and the time required for one analysis is not prolonged vainly. From the same reasons, the measured ionic species of mass 100 u exits from the separation space 5 soon after the beginning of the off-time one period later.

The length $T_O$ of the off-time is set in order that the measured ionic species of mass 400 u may exit from the separation space 5 before the ending of the off-time. More specifically, it is set longer than a time (10μ, and a little) which the measured ionic species of mass 400 u needs additionally to travel through the separation space 5 in comparison to the measured ionic species of mass 100 u. Generally, if $T_O$ is set a little longer than T, the measured ionic species of the mass-to-charge ratio range up to 4 times can be analyzed simultaneously.

Figure 8B:
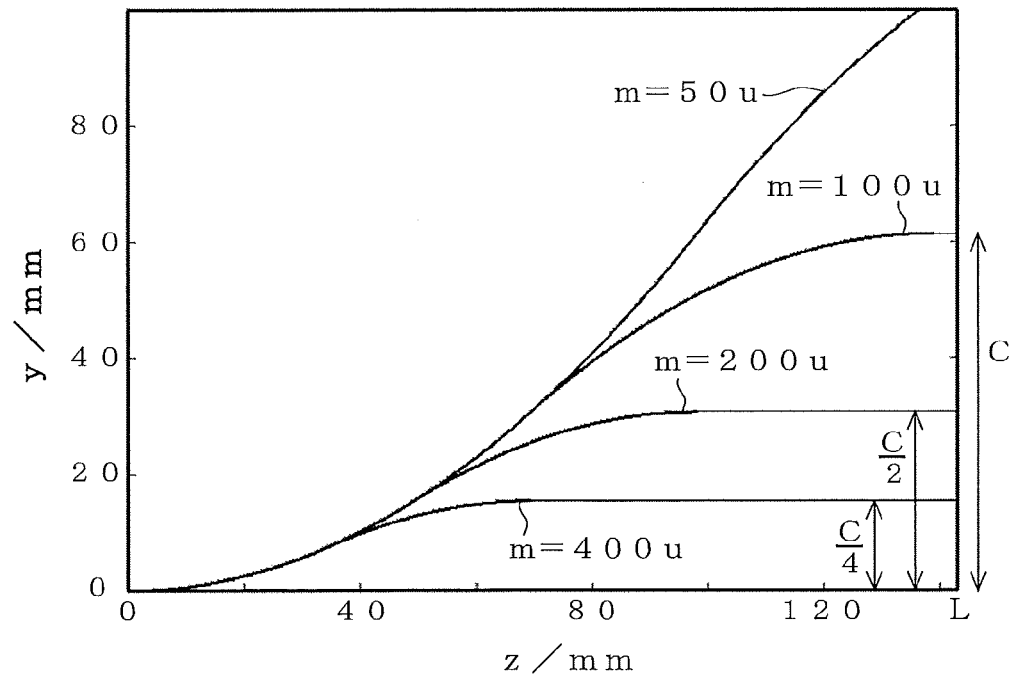
FIG. 8B is a graph which shows trajectories of various ionic species in the above case.

FIG. 8B is a graph which shows trajectories of various ionic species in the case that the multiple measured ionic species are analyzed simultaneously using the above rectangular wave high-frequency electric field. FIG. 8B shows the results obtained by the numerical integrations of the equation of motion (6). We calculated about the case that the charge numbers of ionic species are 1, their masses are 50 u, 100 u, 200 u and 400 u respectively, U is 100 V, T is 10 μs and the strength E of the high-frequency electric field is 2546 $Vm^{-1}$. The trajectories show the flight paths of ions traveling with the standard kinetic energy $z_ieU$ in the z-direction. The bold lines show the flight paths in the high-frequency electric field, whereas the fine lines the flight paths in the off-time. L is the same length as the example shown in FIG. 6. The ion detection unit 4 is constructed to detect ions which come to the position apart from the intersection (0,0) of the baseline 11 and the exit plane 9 by the distance C/4–C (C=61.42 mm) in the y-direction on the plane 9.

The trajectories of the ionic species of mass equal to or smaller than 100 u are the same as shown in FIG. 6A. The displacement magnitude Y of the measured ionic species of mass 100 u is equal to C. The measured ionic species of mass larger than 100 u, for example 200 u or 400 u, have received the action of the high-frequency electric field for one period after the incidence, and meanwhile are displaced by each magnitude Y in the y-direction. Since Y is inversely proportional to the mass-to-charge ratio of the ionic species (see formula (9)), Y is C/2 and C/4 for the ionic species of mass 200 u and 400 u respectively. Then, these ionic species travel comparatively long distances toward the z-direction in the off-time, and arrive at the exit plane 9. By the way, ionic species of mass larger than 400 u (not shown in FIG. 8B) arrive at the exit plane 9 after receiving the action of the high-frequency electric field for a longer time than one period, and the displacement magnitudes y are smaller than C/4.

Thereby, the multiple ionic species of the charge numbers 1 and masses 100-400 u are detected by the ion detection unit 4, and analyzed simultaneously as the measured ionic species. Comparing FIG. 8B with FIG. 6A, we know that the off-time of enough length removes the harmful and useless displacement one period later, and enables the simultaneous analysis of the multiple measured ionic species.

The above is merely an example. The maximum of the mass-to-charge ratio range of the ionic species analyzed simultaneously can be enlarged without limitation in principle, by increasing the length of the off-time $T_O$. The minimum also can be made small without limitation in principle, by decreasing the accelerating voltage U or by shortening the period T. Therefore, the mass spectrometer 10 can get a nearly complete mass spectrum from one introduction of pulsed crude ions in principle, similarly to the TOF mass spectrometer. This feature is particularly effective in the analysis of a single shot phenomenon or a phenomenon rarely occurring, and is suitable for the use of a pulsed ionization method such as matrix-assisted laser desorption ionization. In addition, since the maximum and minimum of the mass-to-charge ratio range measured could be set arbitrary, it is rare that the mass spectrometer 10 measures an unnecessary mass-to-charge ratio range and prolongs the time required for one analysis vainly. This is the feature not to be provided in the TOF mass spectrometer.

Furthermore, when the simultaneous analysis is possible, the mass spectrometer 10 can follow the correct relation among respective amounts of multiple ionic species, and can get accurate and abundant information even in the system where the composition of an analyte changes rapidly. Moreover, the ion availability improves because the ions of the measured ionic species are less wasted without being detected. However, the mass resolution decreases inversely proportional to the mass-to-charge ratio of the measured ionic species, because it is proportional to the displacement magnitude in the mass spectrometer 10.

In the simultaneous analysis, the ion detector have to detect the multiple measured ionic species simultaneously. As such one, we can use an ion detector that has a line- or belt-shaped ion detection area and is able to measure respective amounts of multiple ionic species which come on the different positions in the y-direction. This is, for example, a focal plane detector (array detector), a microchannel plate, etc. At this time, the position resolution on the ion detecting plane can be improved by letting this plane incline to the y-axis.

The focal plane detector is constructed as follows, for example. Ions are converted to electrons and amplified by a microchannel plate, the resultant electrons from the backside of the microchannel plate are then converted to photons by a phosphor screen, and these photons are detected by a photodiode array or a CCD (Charge Coupled Device) detector. In the case with no conversion to photons, the microchannel plate is constructed as follows. Many micro-anodes are prepared with patterning on the backside of the microchannel plate. The above electrons from the backside of the microchannel plate are taken out through these micro-anodes. Thereby, the ion detection area of the microchannel plate is divided to many regions according as the difference in the distance from the baseline 11 in the y-direction, and the amount of ionic species coming on each region is measured individually.

<Design of the Mass Spectrometer>

Let us consider that the change of the displacement magnitude Y→Y−ΔY (ΔY>0) occurs from the change of mass of ions m→m+Δm (Δm>0). From formula (9), we have $$Y - \Delta Y = z_i eET^2/4(m + \Delta m) \quad (24)$$
$$\approx Y(1 - \Delta m/m),$$
$$\Delta m/m \approx \Delta Y/Y.$$

(Strictly, $\Delta Y$ is also reduced by the increase of the stay time. But this reduction was neglected, because this is a small term of higher order.)

Formula (24) means that when the difference $\Delta Y$ cannot be distinguished, the difference $\Delta m$ cannot be distinguished. It is therefore thought that formula (24) gives the mass resolution of the mass spectrometer 10, if $\Delta Y$ stands for the position resolution, namely, the minimum distance which the ion detection unit 4 can distinguish when it detects the measured ionic species in distinction from the neighbouring ionic species based on the y-position. The position resolution is decided by the spread of the ions (the diameter of the ion beam) on the ion detection unit 4, the aperture size of the slit, the structure of the detection area of the ion detector and so on.

We may design the mass spectrometer 10, for example, in the following order.

(1) We decide the displacement magnitude Y of the measured ionic species from the required mass resolution m/$\Delta$m and the realizable position resolution $\Delta Y$ on the ion detection unit 4, using formula (24).

(2) We decide the period T of the high-frequency electric field from the displacement magnitude Y, the mass-to-charge ratio of the measured ionic species and the realizable strength E of the high-frequency electric field, using formula (9).

(3) We decide the effective length L of the separation space 5 and the acceleration voltage U from the period T and the mass-to-charge ratio of the measured ionic species, using formula (18).

The mass spectrometer 10 has many parameters which can be adjusted at the time of design or use. In addition, the displacement magnitude Y and the strength E of the high-frequency electric field are half independent on the effective length L of the separation space 5 and the acceleration voltage U, although the former are related to the latter through the period T. Therefore, it is easy that each parameter is chosen suitable according to the purpose and environment of use and optimal constitution and operation of the mass spectrometer 10 are realized as the combination of these parameters.

Design Example 1

Let the required mass resolution m/$\Delta$m be 300, and the position resolution $\Delta Y$ be 0.2 mm. Then about the next value $$Y=60.0 \text{ mm}$$

is needed from formula (24).

Next, we consider the case that the measured ionic species of the charge numbers 1 and masses 1-200 u should be scanned by the first scan method, and the strength E of the rectangular wave high-frequency electric field should not become too large. For this, for example, about the next value $$T=10 \text{ μs}$$

is preferable for the period T of the high-frequency electric field. In this case, from formula (9), the next value $$E \approx 24.9\text{-}4970 \text{ Vm}^{-1}$$

is needed for E to displace the measured ionic species by the above magnitude Y. (The above range of E corresponds to the mass range 1-200 u of the measured ionic species. The same applies hereafter.) If the distance $L_y$ between the electrodes 6 and 7 is 100 mm, the next value $$V_y \approx 12.49\text{-}497 \text{ V}$$

is needed for the high-frequency voltage $V_y$.

On the other hand, as for the acceleration voltage U and the effective length L of the separation space 5, for example, about the next value $$U=1\text{-}200 \text{ V}$$

is preferable, when it is important that the mass spectrometer 10 is small and light. L is chosen in order that it may satisfy formula (18) for given U. If we substitute above m, U and T into formula (15), we obtain about 139 mm as the length which satisfies formula (15). We make L somewhat longer than it, as much as $T_D + T_E$ is added to T.

Since the above conditions can be easily fulfilled, a small, light and cheap popular-type mass spectrometer can be easily realized with the mass spectrometer 10. Such a mass spectrometer is useful as a gas analyzer etc., for example.

In addition, the above mass spectrometer 10 is also suitable for elementary analysis of a high molecular mass substance. For example, if the measured ionic species of the charge number 1 and mass 5000 u is analyzed with the condition that the accelerating voltage U is 200 V, the period T of the high-frequency electric field is 50 μs and its strength E is 4970 Vm$^{-1}$, the displacement magnitude Y for one period becomes the next value $$Y \approx 60.0 \text{ mm}$$

from formula (9). In this case, since mass resolution becomes 300 as well as the above example, the mass of the measured ionic species is determined in the range of 5000±17 u. This is adequate for the purpose, for example, roughly to determine the degree of polymerization of the high molecular mass substance. It is noteworthy that such a useful datum is obtained with the above simple mass spectrometer 10.

Hitherto, as a mass spectrometer of this field, mostly a quadrupole mass spectrometer has been used. As already described, the quadrupole mass spectrometer has the problems that the transmittance of an ionic species of a large mass-to-charge ratio is low and an ionic species of a larger mass-to-charge ratio than the upper-limit cannot be detected. Hence, there remains fear that some high mass ionic species might be overlooked.

In contrast, in principle the mass spectrometer 10 has no limitation on the mass-to-charge ratio range to be able to deal with. Although its mass resolution may not be enough to separate each ionic species of large mass-to-charge ratios, even in such a case it can be sufficiently presumed what the ionic species are, because their mass-to-charge ratios are determined with high accuracy. Particularly, in the mass spectrometer 10 with the ion detector 15 or 16 shown in FIG. 7B-1 or FIG. 7C, there is no fear that high mass ionic species might be overlooked, because the amount of all ionic species or ionic species of mass-to-charge ratios larger than the measured ionic species is always known.

In addition, the mass spectrometer 10 can measure repeatedly respective amounts of plural ionic species of specific mass-to-charge ratios in a short time by the selected ion scan mode. Therefore, even if there is fluctuation in the ionization conditions in the ion source 1, it is almost compensated by the calibration based on the amount of an internal standard ionic species, without fluctuation arising in the short scanning time. Consequently, quantitative accuracy is not easily lowered. Also, correct relations among respective amounts of plural ionic species can be known even in the system whose composition rapidly changes by fast chemical reactions and so on.

Design Example 2

Let the required mass resolution m/Δm be 2500 and the position resolution ΔY be 0.1 mm. Then about the next value $Y=250.0$ mm is needed from formula (24).

Next, we consider the case that the measured ionic species of the charge numbers 1 and masses 25-1250 u should be scanned by the first scan method, and the strength E of the rectangular wave high-frequency electric field should not become too large. For this, for example, about the next value $T=25$ μs is preferable for the period T of the high-frequency electric field. In this case, from formula (9), the next value $E \approx 414.6\text{-}20700$ $Vm^{-1}$ is needed for E to displace the measured ionic species by the above magnitude Y. If the distance $L_y$ between the electrodes is 300 mm, the next value $V_y \approx 124.4\text{-}6219$ V is needed for the high-frequency voltage $V_y$.

On the other hand, as for the acceleration voltage U and the effective length L of the separation space 5, for example, about the next value $U=20\text{-}1000$ V is preferable, when it is important that the mass spectrometer 10 is small and light. L is chosen in order that it may satisfy formula (18) for given U. If we substitute above m, U and T into formula (15), we obtain about 311 mm as the length which satisfies formula (15). We make L somewhat longer than it, as much as $T_D+T_E$ is added to T.

If the mass-to-charge ratio range is too wide, it may occur that part of values of E become too large or part of values of U become too small only by the first scan method. In this case it is better to use the second scan method together. For example, the measured ionic species of the charge number 1 and masses 1-25 u can be scanned in the above example, as follows. While the strength E of the high-frequency electric field and the acceleration voltage U are fixed to 414.6 $Vm^{-1}$ and 20 V, respectively, the period T of the high-frequency electric field is changed between 5-25 μs. Similarly, the measured ionic species of the charge number 1 and masses 1250-5000 u can be scanned as follows. While the strength E of the high-frequency electric field and the acceleration voltage U are fixed to 20700 $Vm^{-1}$ and 1000 V, respectively, the period T of the high-frequency electric field is changed between 25-50 μs. Thereby, the mass-to-charge ratio range of 1-5000 can be scanned almost continuously with the combination of the two scan method.

The above mass spectrometer 10 can easily realize a small, light, cheap and comparatively high performance mass spectrometer. Furthermore, since it can simultaneously analyze the multiple measured ionic species, it can simultaneously get information about them by one analysis, and the ion availability also improves.

This mass spectrometer 10 is most suitable especially for the mass spectrometer which constitutes GC-MS or LC-MS. In this case, it can measure repeatedly respective amounts of the multiple measured ionic species in a short time, and can get a chromatogram simply. Consequently, it can clarify correct relations among respective amounts of two or more components, even when they elute imperfectly separated. If its ion source 1 is an ion source with the orthogonal accelerator, its ion availability becomes maximumly large. Thereby, GC-MS and LC-MS with high sensitivity are realized.

<Mass Separator>

The mass separator of the present invention, for example, consists of the ion source 1, the ion introduction unit 2, the mass analyzer 3, an ion selection unit, etc. (its illustration is omitted). A passage of ions is in high vacuum at least in the mass analyzer 3 and around it. The ion selection unit, for example, has a block component with a small aperture (a slit 12 etc.) as a means to extract ions which come to the predetermined position in the y-direction on the exit plane 9 (see FIG. 1, FIG. 2 and FIG. 7 about the components with Reference Signs).

This mass separator is the same as the mass spectrometer 10, except that the ion detection unit 4 is replaced by the ion selection unit. The features based on the common constitution are the same as the mass spectrometer 10. Specifically, it is slightly affected by the fluctuation at the initial state of the crude ions in the ion source 1 before extraction, and is able to extract the selected ionic species of a predetermined mass-to-charge ratio from the crude ions with high mass resolution. Consequently, it has little necessity to increase the acceleration voltage in order to attain high mass resolution. As a result, the flight length of ions becomes short, and its instrument becomes small and light. In addition, in principle it has no limitation on the mass-to-charge ratio range to be able to deal with, and can also switch the selected ionic species fast from one to another. It is useful for a first stage mass spectrometer in a tandem mass spectrometer and a first stage in an ion beam instrument.

Embodiment 2

In embodiment 2, we describe an example of the mass spectrometer in which two or more mass analyzers are placed in series, as described in claim 4.

Figure 9A:
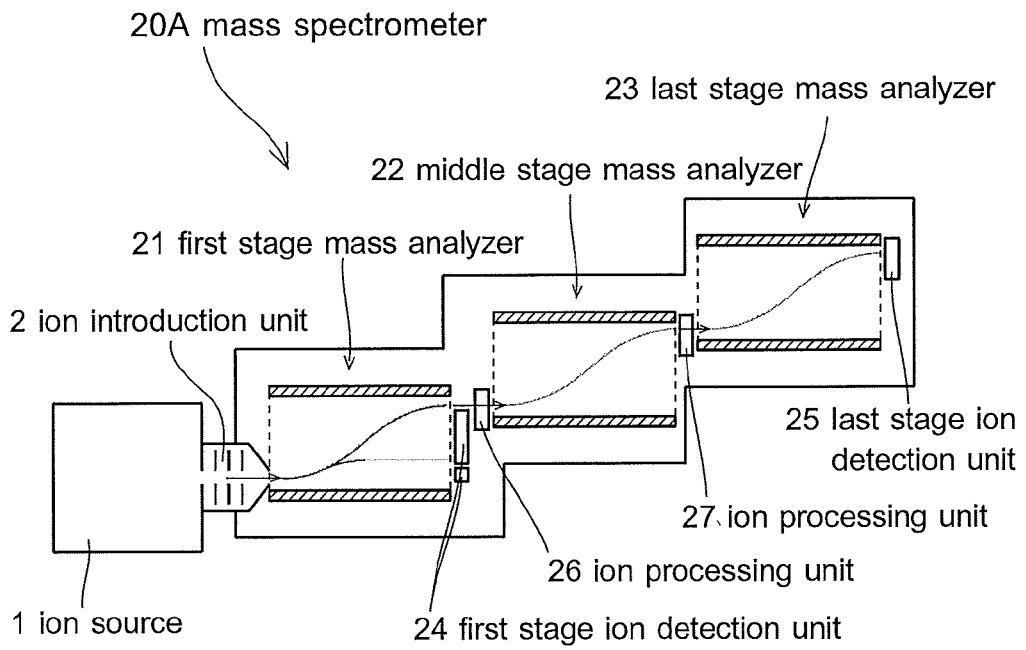
FIG. 9 is a schematic drawing showing the configuration of a mass spectrometer according to embodiment 2 of the present invention.

FIG. 9A is a schematic drawing showing the configuration of a mass spectrometer 20A according to embodiment 2. The mass spectrometer 20A consists of the ion source 1, the ion introduction unit 2, a first stage mass analyzer 21, a middle stage mass analyzer 22, a last stage mass analyzer 23, a first stage ion detection unit 24, a last stage ion detection unit 25, etc. In addition, if necessary, ion processing units 26 and 27 are located between the mass analyzers. These have electrostatic lenses etc. and are equipped for the purpose to improve the convergency of the ions and so on. These also may have a means which re-accelerate or decelerate ions, and be constituted to change the velosities of the measured ionic species which enter into the following mass analyzers 22 and 23 to the optimal velosities fit for each mass analyzer.

The first stage mass analyzer 21 is the same as the mass analyzer 3 described in embodiment 1, and uses the rectangular wave high-requency electric field with off-times as the high-frequency electric field. In the mass spectrometer 20A, the crude ions introduced through the ion introduction unit 2 from the ion source 1 are separated in the first stage mass analyzer 21 at first. Most of the measured ionic species separated are detected by the first stage ion detection unit 24 to be analyzed simultaneously, as we described using FIG. 8. The first stage ion detection unit 24 is one similar to the ion detection unit 4. In this case also, it is desirable that the first stage ion detection unit 24 is equipped with the ion detector 16 and the like, and can measure the amount of ionic species of mass-to-charge ratios larger than the measured ionic species.

The middle stage mass analyzer 22 and last stage mass analyzer 23 are ones similar to the first stage mass analyzer 21. Among the measured ionic species separated, ionic species which require separation with especially high mass resolution are introduced into the following mass analyzers 22 and 23, further separated there with each other, and detected by the last stage ion detection unit 25. The first stage ion detection unit 24 has a small aperture to introduce these ionic species into the middle stage mass analyzer 22. These ionic species travel between the mass analyzers within the off-time of the rectangular wave high-requency electric field. Consequently, the mass analyzers 21-23 are connected without lowering mass resolution, and higher mass resolution is attained by summing up the displacement magnitude Y in each mass analyzer.

In the mass analyzer with the multi-stage constitution like one in the mass spectrometer 20A, the displacement magnitude Y in each stage becomes smaller than the mass analyzer which attains high mass resolution with the single-stage constitution. Consequently, the distance between the electrodes becomes shorter, and the size of the mass analyzer becomes smaller as a whole. In addition, because each mass analyzer operates simultaneously in parallel, the time required for one analysis becomes shorter than the mass analyzer with the single-stage constitution. By the way, the middle stage mass analyzer 22 can be omitted or constituted of two or more mass analyzers, according to required mass resolving power.

We can predict that in the mass spectrometer 20A it is not difficult to realize about 2500 as mass resolution in the first stage mass analyzer 21 and about 7500-10000 as mass resolution in the last stage mass analyzer 23. The whole length of the mass analyzers 21-23 is about 900-1000 mm, and the time required for one analysis is about several ten microseconds. Thus, according to the mass spectrometer 20A, we can not only get a mass spectrum efficiently in a wide mass-to-charge ratio range, but also measure a predetermined mass-to-charge ratio range with higher mass resolution, by a comparatively small instrument.

FIG. 9A shows the example in which among the measured ionic species separated in the first stage mass analyzer 21, ionic species of small mass-to-charge ratios are taken out into the following mass analyzers. Yet the selection is not restricted to it. Ionic species of intermediate mass-to-charge ratios can be taken out and further separated in the following mass analyzers. Thus, we can measure a predetermined mass-to-charge ratio range with higher mass resolution, getting mass spectra in lower and upper mass-to-charge ratio ranges. Ionic species of large mass-to-charge ratios also can be taken out and further separated in the following mass analyzers. Thus, we can improve mass resolution of ionic species of large mass-to-charge ratios, whose mass resolution is comparatively low in the mass analyzer with the single-stage constitution. In this way, we can analyze ionic species in a wide mass-to-charge ratio range with well-matched high mass resolution.

Moreover, two or more groups of the measured ionic species in different mass-to-charge ratio ranges may be taken out, respectively. Then, at least one group is deflected by a static electric field and so on, and following mass analyzers are placed for each group.

Figure 9B:
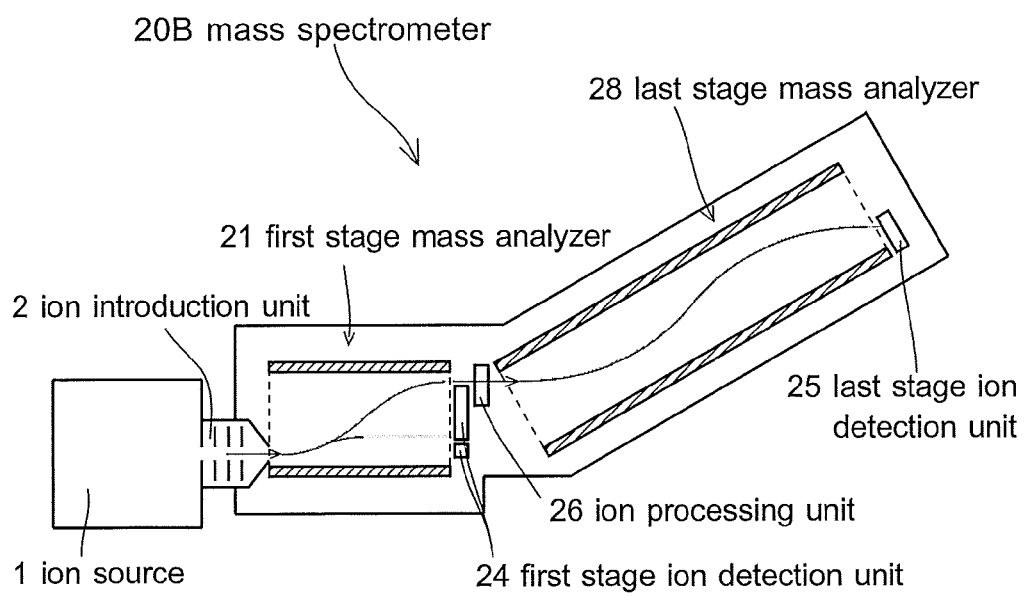

FIG. 9B is a schematic drawing showing the configuration of another mass spectrometer 20B according to embodiment 2. The mass spectrometer 20B consists of the ion source 1, the ion introduction unit 2, the first stage mass analyzer 21, a last stage mass analyzer 28, the first stage ion detection unit 24, the last stage ion detection unit 25, etc. In addition, if necessary, an ion processing unit 29 is located between the mass analyzers.

In the mass spectrometer 20B, the opposite electrodes of the last stage mass analyzer 28 are mounted along the flight path of the measured ionic specie. Consequently, although a large displacement magnitude Y is realized, the distance between the opposite electrodes is not so large. Thereby, the last stage mass analyzer 28 is small for the displacement magnitude Y, and besides the high-frequency voltage applied to the opposite electrodes becomes smaller.

In this case, we need to pay attention to the followings. Not all of the high-frequency electric field acts in the y-direction. The component of the high-frequency electric field which acts in the z-direction displaces ions to the −z-direction, and the flight lengths of the ions in the z-direction become shorter by these displacements. For example, let the last stage mass analyzer 28 be placed as its longitudinal direction inclines 30 degrees to the z-direction of the mass analyzer 21. Using symbol Ed which represents the strength of the high-frequency electric field, the component of strength $(3^{1/2}/2)Ed$ acts to the y-direction, whereas the component of strength $(1/2)Ed$ acts to the −z-direction. Consequently, the displacement $(3^{1/2}/3)$ times as large as the displacement to the y-direction arises to the −z-direction. Therefore, in the last stage mass analyzer 28, if the period is increased, for example, 20-30%, the flight lengths of the ions in the z-direction become the same as the flight lengths in the mass analyzer placed without inclination, when the other conditions are the same. The strength of the high-frequency electric field required to yield the predetermined displacement magnitude in the y-direction becomes smaller also by this increase of the period.

In addition, the placement in which the longitudinal direction of the mass analyzer inclines to the incident direction of the ions as the last stage mass analyzer 28 is equivalent to the oblique incidence where the incident direction inclines toward the y-direction from the longitudinal direction, if viewed from the mass analyzer side. This oblique incidence has the advantages that the mass analyzer becomes smaller and the high-frequency voltage applied to the opposite electrodes becomes smaller as mentioned above, although some restrictions arise about the flight paths of ions. Therefore, in the embodiment 1 also, the mass analyzer 3 may be placed as its longitudinal direction inclines to the incident direction of crude ions, and they enter into the separation space 5 with this oblique incidence.

Embodiment 3

In embodiment 3, we describe an example of the mass spectrometer which unites with a TOF mass spectrometer, and whose separation space is part of the drift path of the TOF mass spectrometer, as described in claim 5.

Figure 10:
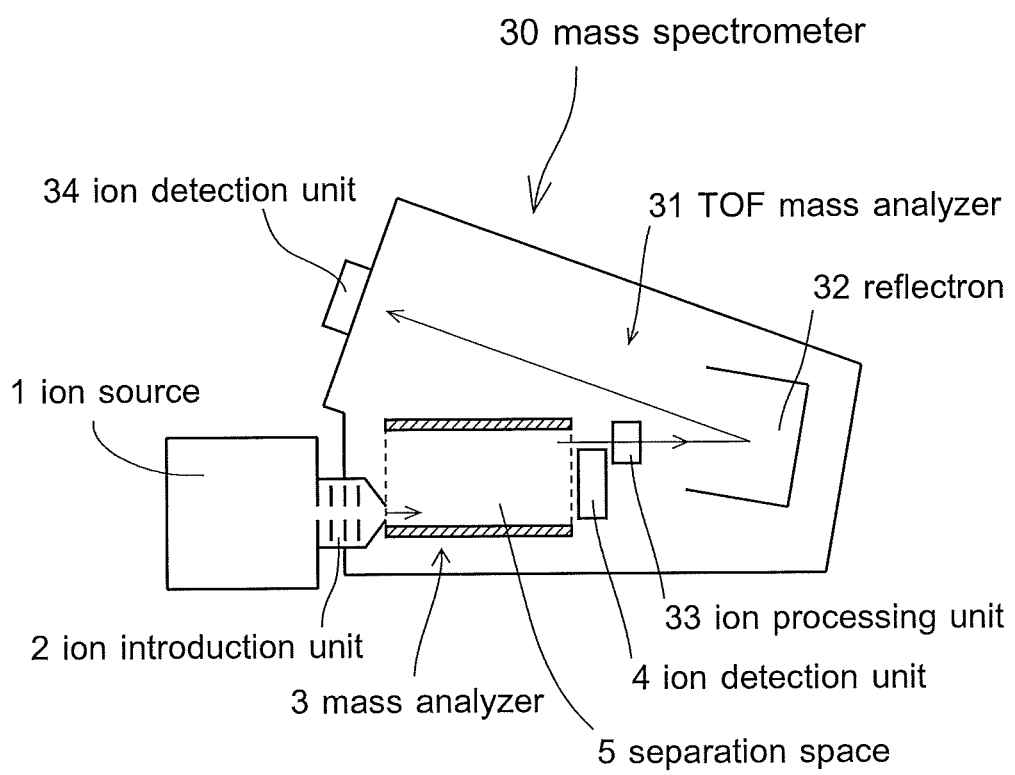
FIG. 10 is a schematic drawing showing the configuration of a mass spectrometer according to embodiment 3 of the present invention.

FIG. 10 is a schematic drawing showing the configuration of a mass spectrometer 30 according to embodiment 3. The mass spectrometer 30 consists of the ion source 1, the ion introduction unit 2, the mass analyzer 3, the ion detection unit 4, a TOF mass analyzer 31, a reflectron 32, an ion detection unit 34, etc. In addition, if necessary, an ion processing unit 33 is located. This has an electrostatic lens etc. and is equipped for the purpose to improve the convergency of the ions and so on. This also may have a means which re-accelerates ions, and be constituted to change the velosities of the ionic species which continue traveling in the TOF mass analyzer 31 to the optimal velosities. Generally, the condition which is desirable when crude ions travel in the mass analyzer 3 may not agree with the condition which is desirable when they travel in the TOF mass analyzer 31. The ion processing unit 33 coordinates the difference between these conditions.

The feature of the mass spectrometer 30 is that the separation space 5 of the mass analyzer 3 is mounted to share the space with part of the drift path of the TOF mass analyzer 31. The ion source 1, the ion introduction unit 2, the mass analyzer 3, and the ion detection unit 4 constitute the mass spectrometer 10 described in embodiment 1. On the other hand, the ion source 1, the ion introduction unit 2, the TOF mass analyzer 31, the reflectron 32, the ion processing unit 33, and the ion detection unit 34 constitute the reflectron TOF mass spectrometer. Both unite in the mass spectrometer 30.

In the mass spectrometer 30, the crude ions are introduced from the ion source 1 through the ion introduction unit 2 and separated in the mass analyzer 3. Most of the measured ionic species separated are detected by the ion detection unit 4 to be analyzed simultaneously, as we described using FIG. 8. Among the measured ionic species separated, ionic species which require separation with especially high mass resolution continue traveling on the residual drift path of the TOF mass analyzer 31, and are detected by the ion detection unit 34. By the way, FIG. 10 shows the example that the drift path of the TOF mass analyzer 31 is in the yz-plane, but it may be in the xz-plane.

FIG. 10 shows the example in which among the measured ionic species, ionic species of small mass-to-charge ratios are taken out and analyzed in the TOF mass spectrometer. Yet the selection is not restricted to it. Ionic species of intermediate or large mass-to-charge ratios can be analyzed in the TOF mass spectrometer, similarly to embodiment 2.

According to the mass spectrometer 30, we can not only get a mass spectrum efficiently in a wide mass-to-charge ratio range, but also measure a predetermined mass-to-charge ratio range with higher mass resolution. Comparing with the mass spectrometer 20, the mass spectrometer 30 has the advantage that even when it realizes the highest level mass resolution, detection sensitivity may not be easily lowered, because it has the TOF mass spectrometer instead of the middle and last mass analyzer.

On the other hand, comparing with a usual TOF mass spectrometer, the mass spectrometer 30 has the great advantage that ionic species other than the measured ionic species analyzed with the TOF mass spectrometer are removed from the drift path of the TOF mass analyzer 31 by the mass analyzer 3. Consequently, the mass spectrometer 30 need not wait for the next introduction of crude ions until all ionic species introduced by the previous pulse travel through the drift path. It can introduce pulsed crude ions one after another according to the repetition of the rectangular wave high-frequency electric field, and can get TOF mass spectra repeatedly at intervals of about several ten microseconds.

In the case that we place the mass analyzer 3 principally to remove some ionic species from the flight path of the TOF mass analyzer 31, we can replace the ion detection unit 4 by an ion selection unit. In this case, the ion source 1, the ion introduction unit 2, the mass analyzer 3, and the ion selection unit constitute the mass separator of the present invention.

Embodiment 4

In embodiment 4, we describe an example of the mass spectrometer described in claim 6.

Figure 11A:
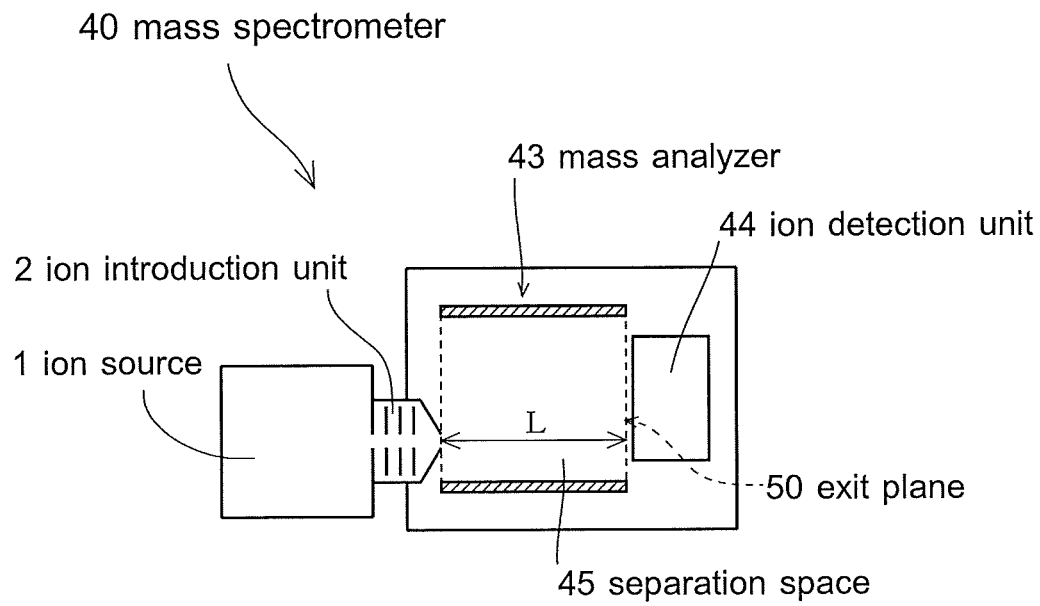
FIG. 11A is a schematic drawing showing the configuration of a mass spectrometer according to embodiment 4 of the present invention.

FIG. 11A is a schematic drawing showing the configuration of a mass spectrometer 40 according to embodiment 4. The mass spectrometer 40 consists of the ion source 1, the ion introduction unit 2, a mass analyzer 43, an ion detection unit 44, etc.

Figure 11B:
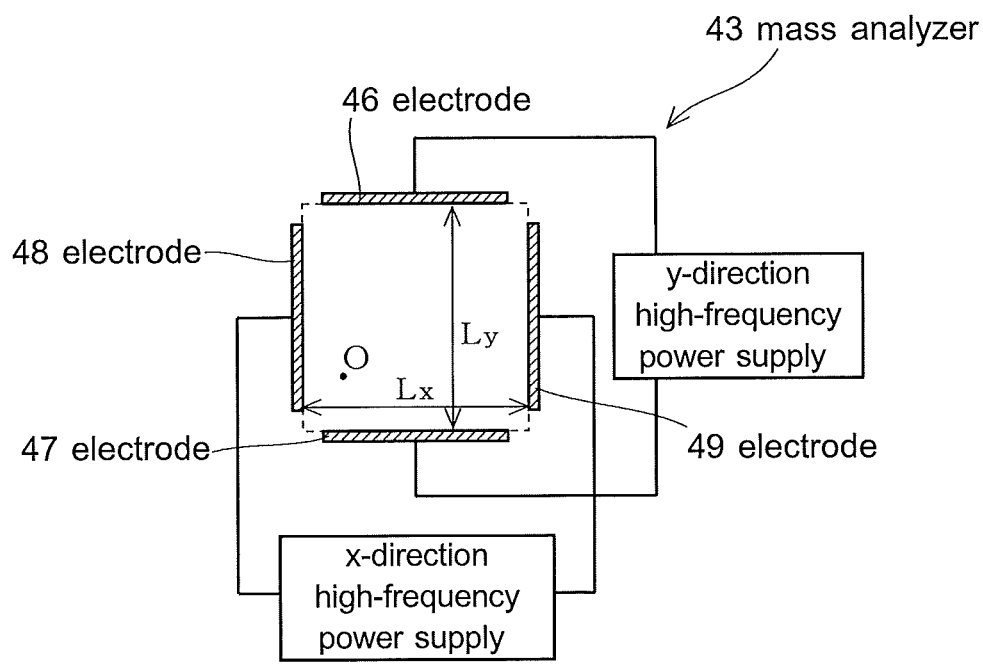
FIG. 11B is a schematic drawing showing the cross-sectional view which cut the mass analyzer in FIG. 11A, perpendicular to the longitudinal direction.

FIG. 11B is a schematic drawing showing the cross-sectional view which cut the mass analyzer 43 perpendicular to the longitudinal direction. In the mass analyzer 43, electrodes 46-49 similar to the electrodes 6 and 7 shown in FIG. 2 are located at the top and bottom and both sides of the separation space 45. The principal planes of these electrodes are perpendicular to the y-axis or x-axis. Y-direction high-frequency voltage is applied between the electrodes 46 and 47, and x-direction high-frequency voltage is applied between the electrodes 48 and 49. Then the high-frequency electric fields are produced in the y-direction and x-direction, respectively.

Two high-frequency electric fields are both produced in the separation space 45, but conceptually these function individually. It is possible because of the following reason. If an ion enters into the separation space after ¼ or ¾ period from the rising of the one-dimensional high-frequency electric field, the rate and magnitude of its displacement becomes 0 at the time when it has received the action of the electric field for one period (see formula (8) and FIG. 3B). It is therefore intelligible to regard the mass spectrometer 40 as one in which two mass analyzers are placed to overlap sharing the separation space 45.

Figure 12A:
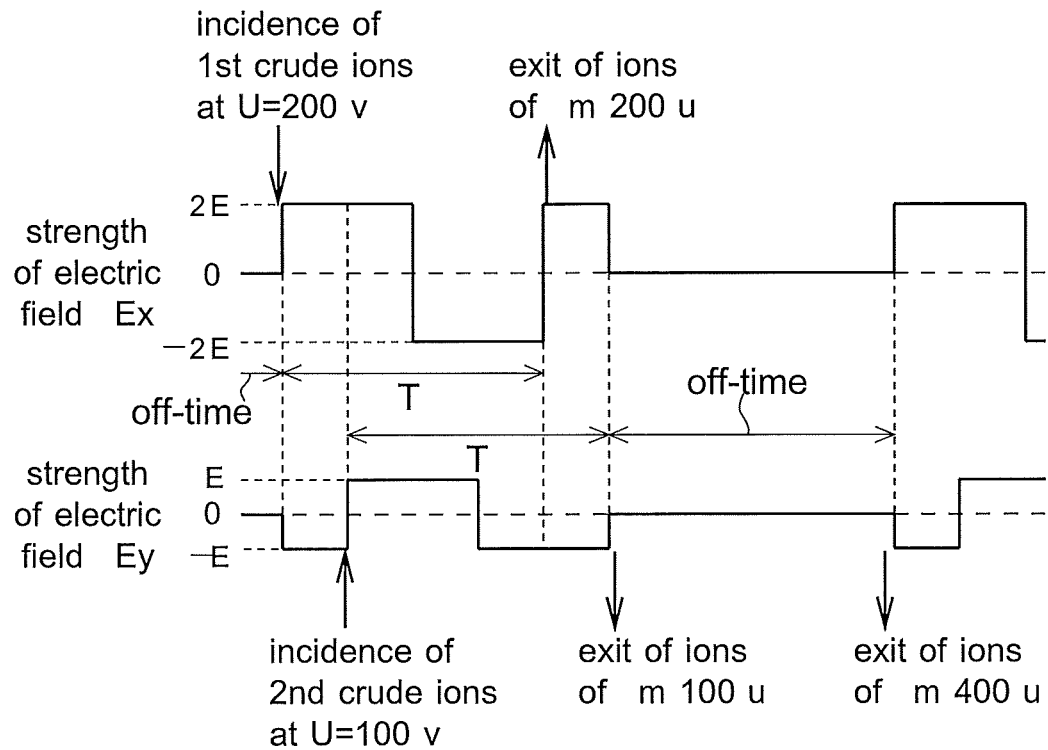
FIG. 12A is a graph showing an example of the rectangular wave high-frequency electric field which is used in the mass spectrometer shown in FIG. 11A.

FIG. 12A is a graph showing an example of the high-frequency electric field which is used in the mass spectrometer 40. The 1st and 2nd crude ions are introduced in a pulsed manner at an interval of approximately ¼ period at different acceleration voltages. This high-frequency electric field enables analysis of one measured ionic species in the 1st crude ions and simultaneous analysis of the multiple measured ionic species in the 2nd crude ions.

The 2nd crude ions are separated by the y-direction high-frequency electric field. This electric field is essentially the same as the rectangular wave high-frequency electric field shown in FIG. 8A. It continues one period from the rising, and then enters into the off-time. The length of the off-time is decided according to the mass-to-charge ratio range of the measured ionic species simultaneously analyzed. Different from the electric field shown in FIG. 8A, however, before the rising it has ¼ period in which the y-direction electric field acts, in order that it may not affect the mass separation of the 1st crude ions. The 2nd crude ions are introduced in a pulsed manner immediately before the rising of the y-direction high-frequency electric field.

The 1st crude ions are separated by the x-direction high-frequency electric field. This electric field has the same period as the y-direction electric field, and its rising precedes the rising of the y-direction electric field for ¼ period. It rises from the off-time, continues (1+¼) period, and then enters again into the off-time. This duration consists of one period to separate the 1st crude ions and ¼ period not to affect the separation of the 2nd crude ions. The 1st crude ions are introduced in a pulsed manner immediately before the rising of the x-direction high-frequency electric field.

Figure 12B:
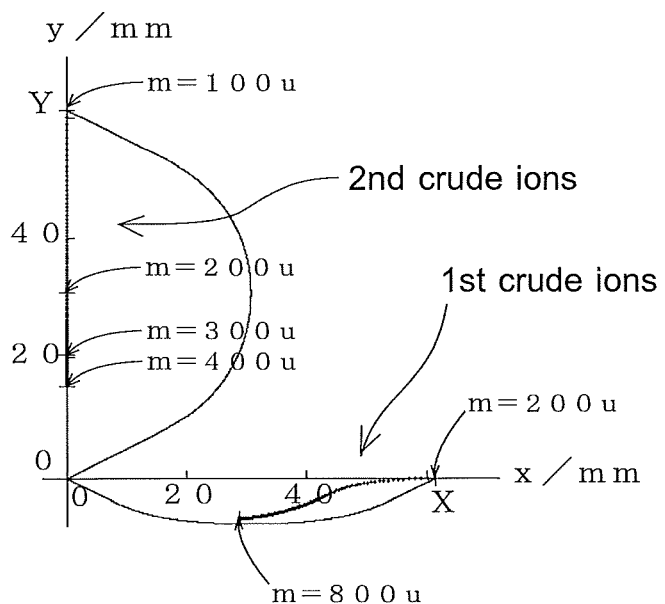
FIG. 12B is a plane view showing the positions of ionic species which come on the exit plane of the mass analyzer shown in FIG. 11A.

FIG. 12B is a plane view showing the positions of ionic species which come on the exit plane 50 of the mass analyzer 43. In the figure, the positions of the 1st and 2nd crude ions show the results obtained by calculations. For the 2nd crude ions, we calculated about the case that the period T and strength E of the y-direction high-frequency electric field are 10 µs and 2546 Vm$^{-1}$ respectively, the acceleration voltage U is 100 V, and the effective length L of the separation space 45 is somewhat longer than 138.91 mm, the same as the case shown in FIG. 8. In contrast, for the 1st crude ions, we calculated about the case that the strength of the x-direction high-frequency electric field is 2E (5092 Vm$^{-1}$) and the acceleration voltage is somewhat larger than 200 V.

Similarly to the case we described using FIG. 8, the measured ionic species of the charge numbers 1 and masses 100-400 u in the 2nd crude ions have received the action of the y-direction high-frequency electric field for one period, are displaced by each magnitude Y in the y-direction, exit from the separation space 45 within the off-time, and are analyzed simultaneously. The positions to which these measured ionic species come on the y-axis are shown at mass intervals of 2 u in FIG. 12B (the y-coordinates were calculated using formula (9)). The displacement magnitude Y of the measured ionic species of mass 100 u is about 61.42 mm. The positions of ionic species of the charge numbers 1 and masses larger than 400 u are below and deviate from the y-axis (not shown in FIG. 12B).

One fine curve near the y-axis in FIG. 12B shows the trajectry on the xy-coordinates on which the ionic species of the charge number 1 and mass 100 u travels in one period after the incidence. (We calculated the y-coordinates by integrating the equation of motion (6) numerically. We calculated the x-coordinates by substituting the above x-direction high-frequency electric field into the similar equation of motion about the displacement magnitude x and integrating the equation numerically.) Because the electric field also acts in the x-direction, the trajectry deviates from the y-axis on the way, but the displacement magnitude x becomes 0 one period later. The other measured ionic species also travel on the similar trajectories (not shown in FIG. 12B). This is because the incident time of the 2nd crude ions is after ¼ period from the rising of the x-direction electric field. In addition, this is because the rates of the displacement in the x-direction become 0 one period later and these halting states are kept throughout the off-time. Thereby, the x-direction electric field does not disturb the mass separation of the measured ionic species in the 2nd crude ions.

On the other hand, the acceleration voltage is set somewhat larger than 200 v in the 1st crude ions, according to that the effective length L of the separation space 45 is somewhat longer than 138.91 mm Thereby, the ionic species of the charge number 1 and mass 200 u exits from the separation space 45 as the measured ionic species, at the time when it has received the action of the x-direction electric field for one period or for the substantially same time as it. Therefore, this ionic species can be detected with little reduction of mass resolution due to the fluctuation at the initial state, if an ion detector similar to the ion detector 13 is located at the position where it comes on in the x-direction. Here, its displacement magnitude X one period later is about 61.42 mm.

The other fine curve near the x-axis in FIG. 12B shows the trajectry on the xy-coordinates on which this measured ionic species travels in one period after the incidence (We calculated it similarly to the above trajectory of the measured ionic species in the 2nd crude ions.). Because the electric field also acts in the y-direction, the trajectry deviates from the x-axis on the way, but the displacement magnitude y becomes 0 one period later. This is because the incident time of the 1st crude ions is before ¼ period (equivalent to after ¾ period) from the rising of the y-direction electric field. Thereby, the y-direction electric field does not disturb the mass separation of the measured ionic species in the 1st crude ions. For reference, the main positions to which ionic species of the charge numbers 1 and masses 204-800 u in the 1st crude ions come are shown at mass intervals of 4 u in FIG. 12B. The positions deviate from the x-axis, because each of these ionic species receives the action of the y-direction electric field for a time at most ¼ period longer than one period.

Here, if the strength of the x-direction electric field is the same as the strength of the y-direction electric field, the displacement magnitude X of the measured ionic species of mass 200 u in the 1st crude ions becomes a half of the displacement magnitude Y of the measured ionic species of mass 100 u in the 2nd crude ions. Hence mass resolution also becomes a half. Accordingly, the strength of the x-direction electric field was made into twice the strength of the y-direction electric field in this example. Thereby, the displacement magnitude become the same in both measured ionic species, we can measure both with the same mass resolution.

Figure 13:
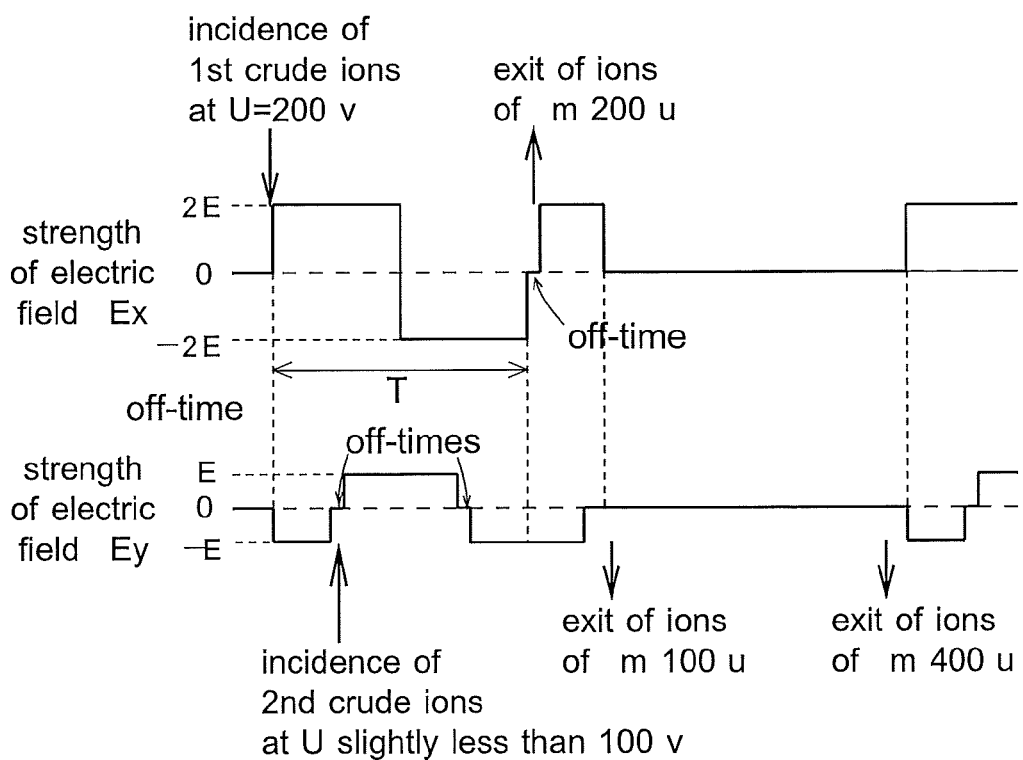
FIG. 13 is a graph showing another variation of the rectangular wave high-frequency electric field which is used in the mass spectrometer shown in FIG. 11A.

FIG. 13 is a graph showing another example of the high-frequency electric field, in which the rectangular high-frequency electric field shown in FIG. 12A is somewhat modified. This y-direction high-frequency electric field has short off-times at the rising and falling. The 2nd crude ions are introduced within the off-time before the rising. Consequently, the 2nd crude ions are not affected by the fringe field. In this case, the length of a time when the y-direction electric field acts becomes shorter by the off-times. It is therefore necessary somewhat to strengthen the y-direction electric field to obtain the same displacement magnitude.

This x-direction high-frequency electric field has a short off-time between one period and the residual ¼ period. The measured ionic species exit within this off-time. In this case, by the already described effects of the off-time, the mass separation becomes less affected by the fluctuation at the initial state, and higher mass resolution is obtained. In addition, simultaneous analysis of the multiple measured ionic species in the 1st crude ions becomes possible, although their mass-to-charge ratio range is limited. Furthermore, the measured ionic species are not affected by the fringe field.

Because of this off-time, however, the displacement magnitude x of the measured ionic species in the 2nd crude ions in the x-direction becomes not 0, when they exit from the separation space. It is not desirable therefore that the length of this off-time is unnecessarily long. Here, according to this off-time, the measured ionic species in the 1st and 2nd crude ions must stay for a somewhat longer stay times in the separation space 45. Therefore the acceleration voltages of these crude ions should be somewhat decreased respectively.

In the mass spectrometer 40, the mass-to-charge ratios of the measured ionic species can be independently set for two groups of pulsed crude ions introduced at a short interval. These measured ionic species can be analyzed with the same mass resolution. This interval is approximately ¼ period, and is a short time of about 2.5 μs. In addition, the multiple measured ionic species of arbitrary mass-to-charge ratio range can be simultaneously analyzed in the 2nd crude ions. The measured ionic species may be confined to one or several species in the 1st crude ions. It is enough, however, when this measured ionic species is the internal standard ionic species, and respective amounts of the measured ionic species in the 2nd crude ions are calibrated based on its amount. Thereby, quantitative accuracy is simply realized in the mass spectrometer 40.

As above, we have described the present inventions according to the respective embodiments. It is needless to say that the present inventions are not limited to these examples whatever, appropriate modifications may be made on them within the scope of the claimed inventions.

INDUSTRIAL APPLICABILITY

The present inventions enhance usefulness which the mass spectrometer and mass separator have in research and application of chemistry, physics, biology, medicine and so on, and contribute to these devices spreading further.

REFERENCE SIGNS LIST 1 ion source, 2 ion introduction unit, 3 mass analyzer, 4 ion detection unit, 5 separation space, 6,7 electrodes, 6a,7a principal planes of electrodes 6,7, 8 incident plane, 9 exit plane, 10 mass spectrometer, 11 base line, 12a upper slit, 12b lower slit, ion detector, 14 blocking plate, 15,16 ion detectors, 17 electrostatic lens, 20A,20B mass spectrometers, 21 first stage mass analyzer, 22 middle stage mass analyzer, 23 last stage mass analyzer, first stage ion detection unit, 25 last stage ion detection unit, 26,27 ion processing units, 28 last stage mass analyzer, 29 ion processing unit, 30 mass spectrometer, 31 TOF mass analyzer, 32 reflectron, 33 ion processing unit, 34 ion detection unit, 40 mass spectrometer, 43 mass analyzer, 44 ion detection unit, 45 separation space, 46-49 electrodes, 50 exit plane

PRIOR ART DOCUMENTS

Non Patent Literature

Non patent Literature 1: Michisato Toyoda, "Shitsuryō-bunseki," in "Zikken-kagaku Kōza 20-1; Bunseki-kagaku," 5th ed, ed by The Chemical Society of Japan, Maruzen, 2007, Chap. 9

Non patent Literature 2: Jürgen H. Gross, "Mass Spectrometry; A Textbook", Springer-Verlag, 2007

Non patent Literature 3: Edmond de Hoffmann and Vincent Stroobant, "Mass Spectrometry; Principles and Applications", Wiley-Interscience, 2007

Non patent Literature 4: K. Fuwa and T. Fujii, "Shijūkyoku shituryō-bunseki-kei; Genri to Ōyō", Kōdansha, 1977

The invention claimed is:

1. A mass spectrometer comprising at least:
an ion source having a means to ionize a sample, and a means to introduce pulsed crude ions into a mass analyzer by a predetermined acceleration voltage;
an ion introduction unit having a means to focus the flight directions of said crude ions, and/or a means to select out said crude ions which travel toward predetermined directions;
said mass analyzer which has a separation space where said crude ions introduced travel and a means to produce in said separation space a one-dimensional high-frequency electric field that acts in the direction (hereafter referred to as y-direction) crossing the incident direction of said crude ions at a predetermined angle, and makes the ionic species having different mass-to-charge ratios with each other travel on different flight paths through the action of said one-dimensional high-frequency electric field;
an ion detection unit having a means to detect ions which come to the predetermined position in the y-direction on the exit plane at the end of said separation space;
wherein said crude ions are introduced into said separation space as a pulse synchronized with the phase of said one-dimensional high-frequency electric field, and the measured ionic species of a predetermined mass-to-charge ratio(s) exits from said separation space having received the action of said one-dimensional high-frequency electric field for n periods or for the substantially same time as it, and is detected in distinction from the other ionic species based on the position in the y-direction on said exit plane (Here, n stands for a natural number.).

2. The mass spectrometer of claim 1, wherein said measured ionic species satisfies the next relation $$T=L(m/2z_i eU)^{1/2},$$

and said crude ions are introduced into said separation space when the strength of said one-dimensional high-frequency electric field is 0, and said measured ionic species exits from said separation space while the electric field strength is substantially 0 one period later. (Here, $z_i$ is the charge number of an ionic species, and m, e, U, L and T are mass of this ionic species, the elementary charge, said acceleration voltage, the effective length of said separation space and the period of said one-dimensional high-frequency electric field, respectively, which are expressed in the SI units. In addition, the effective length of said separation space is the length of the section where said crude ions travel receiving the action of said one-dimensional high-frequency electric field).

3. The mass spectrometer of claim 1, wherein said one-dimensional high-frequency electric field has off-times before and after one period, in which the electric field strength is 0, said measured ionic species satisfies the next relation $$T+T_P<T_L<T+T_P+T_O,$$

said crude ions are introduced into said separation space within a former off-time, and said measured ionic species exits from said separation space within a latter off-time. (Here, $T_L$, $T_P$ and $T_O$ are each times needed for ions of said measured ionic species to travel through said effective length of said separation space, a time from the incident time of said crude ions to the beginning of the period, and the length of the latter off-time, which are expressed in the SI units).

4. The mass spectrometer of claim 3, wherein two or more said mass analyzers are placed in series, said crude ions are separated in the first stage mass analyzer at first, part of said measured ionic species separated are detected by said ion detection unit, and the others are introduced into the following mass analyzers to be further separated there and detected by another ion detection unit located in the downstream side.

5. The mass spectrometer of claim 3, which unites with a time-of-flight (TOF) mass spectrometer, and whose separation space is also part of the drift path of said TOF mass spectrometer, and in which said crude ions are introduced into said separation space and separated in said mass analyzer at first, part of said measured ionic species separated are detected by said ion detection unit, and the others continue traveling on said drift path and are analyzed by said TOF mass spectrometer.

6. The mass spectrometer of claim 1, wherein said mass analyzer has a means to produce in said separation space a x-direction high-frequency electric field whose period is substantially the same as said one-dimensional high-frequency electric field (hereafter referred to as y-direction electric field), and whose phase is different substantially by ¼ period from the y-direction electric field, and which acts in the direction (hereafter referred to as x-direction) crossing the incident direction of said crude ions at a predetermined angle and perpendicular to the y-direction;

said ion detection unit has a means to detect ions which come to the predetermined position in the x-direction on said exit plane;

said crude ions are introduced into said separation space at or immediately before the rising of the y-direction electric field, and said n is 1;

another group of crude ions are introduced into said separation space as a pulse at or immediately before the rising of the x-direction electric field, and the measured ionic species of a predetermined mass-to-charge ratio(s) in this group exits from said separation space having received the action of the x-direction electric field for one period or for the substantially same time as it, and is detected in distinction from the other ionic species based on the position in the x-direction on said exit plane.

7. The mass spectrometer of claim 1, wherein the waveform of said one-dimensional high-frequency electric field is one of a rectangular wave, a sine wave (equivalent to a cosine wave), a step-wise wave, a trapezoidal wave, a triangular wave, a saw-tooth wave, a waveform in which one of these is partly modified, and a waveform in which two or more of these are composed.

8. The mass spectrometer of claim 1, wherein the scan is performed by fixing the period of said one-dimensional high-frequency electric field and changing the acceleration voltage.

9. The mass spectrometer of claim 1, wherein the scan is performed by fixing the acceleration voltage and changing the period of said one-dimensional high-frequency electric field.

10. The mass spectrometer of claim 1, wherein said ion detection unit has an ion detector which detects ionic species of mass-to-charge ratios larger than said measured ionic species, together with or separately from the measured ionic species.

11. A mass separator comprising at least:

an ion source having a means to ionize a sample, and a means to introduce pulsed crude ions into a mass analyzer by a predetermined acceleration voltage;

an ion introduction unit having a means to focus the flight directions of said crude ions, and/or a means to select out said crude ions which travel toward predetermined directions;

said mass analyzer which has a separation space where said crude ions introduced travel and a means to produce in said separation space a one-dimensional high-frequency electric field that acts in the direction (hereafter referred to as y-direction) crossing the incident direction of said crude ions at a predetermined angle, and makes the ionic species having different mass-to-charge ratios with each other travel on different flight paths through the action of said one-dimensional high-frequency electric field;

an ion selection unit having a means to extract ions which come to the predetermined position in the y-direction on the exit plane at the end of said separation space;

wherein said crude ions are introduced into said separation space as a pulse synchronized with the phase of said one-dimensional high-frequency electric field, and the selected ionic species of a predetermined mass-to-charge ratio(s) exits from said separation space having received the action of said one-dimensional high-frequency electric field for one period or for the substantially same time as it, and is extracted in distinction from the other ionic species based on the position in the y-direction on said exit plane.

* * * * *